United States Patent
Newkirk et al.

(12)
(10) Patent No.: US 6,417,121 B1
(45) Date of Patent: *Jul. 9, 2002

(54) MULTICOMPONENT FIBERS AND FABRICS MADE USING THE SAME

(75) Inventors: David D. Newkirk; Harold Edward Thomas, both of Greer; David Bruce Christopher, Simpsonville; Barry DeWayne Meece, Pelzer, all of SC (US)

(73) Assignee: BBA Nonwovens Simpsonville, Inc., Simpsonville, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/476,067

(22) Filed: Dec. 30, 1999

Related U.S. Application Data

(63) Continuation-in-part of application No. 08/997,082, filed on Dec. 23, 1997, now abandoned, which is a continuation of application No. 08/676,360, filed on Aug. 27, 1996, now Pat. No. 5,804,286, which is a continuation-in-part of application No. 08/344,419, filed on Nov. 23, 1994, now abandoned, which is a continuation-in-part of application No. 08/344,731, filed on Nov. 23, 1994, now abandoned, which is a continuation-in-part of application No. 08/344,732, filed on Nov. 23, 1994, now Pat. No. 5,543,206.

(51) Int. Cl.$^7$ .............. D01F 8/00; D01F 8/06; D04H 3/00; D04H 3/14

(52) U.S. Cl. ........ 442/364; 442/361; 442/381; 442/382; 442/392; 442/394; 442/328; 428/373; 428/365; 428/198; 604/358

(58) Field of Search .................. 442/361, 364, 442/381, 382, 392, 394, 328, 401, 400, 409; 428/364, 365, 373, 198; 525/240; 604/358, 366, 378

(56) References Cited

U.S. PATENT DOCUMENTS

| | | | |
|---|---|---|---|
| 3,595,731 A | 7/1971 | Davies et al. |
| 3,807,917 A | 4/1974 | Shimoda et al. |
| 4,153,664 A | 5/1979 | Sabee |
| 4,223,063 A | 9/1980 | Sabee |
| 4,251,200 A | 2/1981 | Parkin |
| 4,525,407 A | 6/1985 | Ness |
| 4,563,504 A | 1/1986 | Hert et al. |
| 4,632,861 A | 12/1986 | Vassilatos |
| 4,634,739 A | 1/1987 | Vassilatos |
| 4,644,045 A | 2/1987 | Fowells |
| 4,717,325 A | 1/1988 | Fujimura et al. |
| 4,769,279 A | 9/1988 | Graham |

(List continued on next page.)

FOREIGN PATENT DOCUMENTS

| | | |
|---|---|---|
| CA | 1 193 395 | 9/1985 |
| CA | 1 199 746 | 1/1986 |
| EP | 394954 | 10/1990 |
| EP | 405793 | 1/1991 |
| EP | 416620 | 3/1991 |
| EP | 445536 | 9/1991 |
| EP | 516412 | 12/1992 |
| EP | 621 356 | 10/1994 |
| JP | 63-243324 | 10/1988 |
| WO | WO 90/10672 | 9/1990 |
| WO | WO 93/15251 | 8/1993 |
| WO | WO 96/16216 | 5/1996 |
| WO | WO 00/28122 | 5/2000 |

Primary Examiner—Cheryl A. Juska
(74) Attorney, Agent, or Firm—Alston & Bird LLP

(57) ABSTRACT

The present invention provides multicomponent fibers arranged in structured domains. At least one of the polymer components is formed of a multipolymer blend. The present invention also provides nonwoven fabrics formed of the multicomponent fibers, the fabrics having a superior combination of extensibility, tensile properties and abrasion resistance. A second layer can be laminated to this coherent extensible nonwoven web.

46 Claims, 7 Drawing Sheets

U.S. PATENT DOCUMENTS

| | | | | |
|---|---|---|---|---|
| 4,770,925 A | | 9/1988 | Uchikawa et al. | |
| 4,822,678 A | | 4/1989 | Brody et al. | |
| 4,834,741 A | | 5/1989 | Sabee | |
| 4,839,228 A | | 6/1989 | Jezic et al. | |
| 4,842,922 A | | 6/1989 | Krupp et al. | |
| 4,874,666 A | | 10/1989 | Kubo et al. | |
| 4,908,052 A | | 3/1990 | Largman et al. | |
| 4,910,064 A | | 3/1990 | Sabee | |
| 4,938,832 A | | 7/1990 | Schmalz | |
| 5,068,141 A | | 11/1991 | Kubo et al. | |
| 5,108,827 A | | 4/1992 | Gessner | |
| 5,114,781 A | | 5/1992 | Mormon | |
| 5,116,662 A | | 5/1992 | Mormon | |
| 5,185,199 A | | 2/1993 | Sawyer et al. | |
| 5,240,764 A | | 8/1993 | Haid et al. | |
| 5,242,436 A | | 9/1993 | Weil et al. | |
| 5,254,299 A | | 10/1993 | Krupp et al. | |
| 5,294,482 A | * | 3/1994 | Gessner | 428/287 |
| 5,334,446 A | | 8/1994 | Quantrille et al. | |
| 5,405,682 A | * | 4/1995 | Shawyer et al. | 428/221 |
| 5,425,987 A | | 6/1995 | Shawver et al. | |
| 5,470,639 A | | 11/1995 | Gessner et al. | |
| 5,482,772 A | | 1/1996 | Strack et al. | |
| 5,487,943 A | | 1/1996 | Kozulla | |
| 5,503,907 A | * | 4/1996 | Gessner et al. | 428/198 |
| 5,536,555 A | | 7/1996 | Zelazoski et al. | |
| 5,543,206 A | * | 8/1996 | Austin et al. | 428/198 |
| 5,554,437 A | * | 9/1996 | Gupta et al. | 428/286 |
| 5,573,768 A | | 11/1996 | Gessner | |
| 5,582,667 A | * | 12/1996 | Gupta et al. | 156/148 |
| 5,593,768 A | | 1/1997 | Gessner | |
| 5,607,798 A | | 3/1997 | Kobylivker et al. | |
| 5,631,083 A | | 5/1997 | Pinoca et al. | |
| 5,645,057 A | | 7/1997 | Watt et al. | |
| 5,804,286 A | | 9/1998 | Quantrille et al. | |
| 5,921,973 A | * | 7/1999 | Newkirk et al. | 604/365 |
| 6,015,617 A | | 1/2000 | Maugans et al. | |
| 6,207,602 B1 | * | 3/2001 | Gessner et al. | 442/363 |
| 6,225,243 B1 | * | 5/2001 | Austin | 442/361 |
| 2001/0003693 A1 | * | 6/2001 | Gessner et al. | 442/363 |
| 2001/0004574 A1 | * | 6/2001 | Gessner et al. | 442/363 |
| 2001/0005662 A1 | * | 6/2001 | Gessner et al. | 442/290 |
| 2001/0008675 A1 | * | 7/2001 | Meece et al. | 428/103 |

* cited by examiner

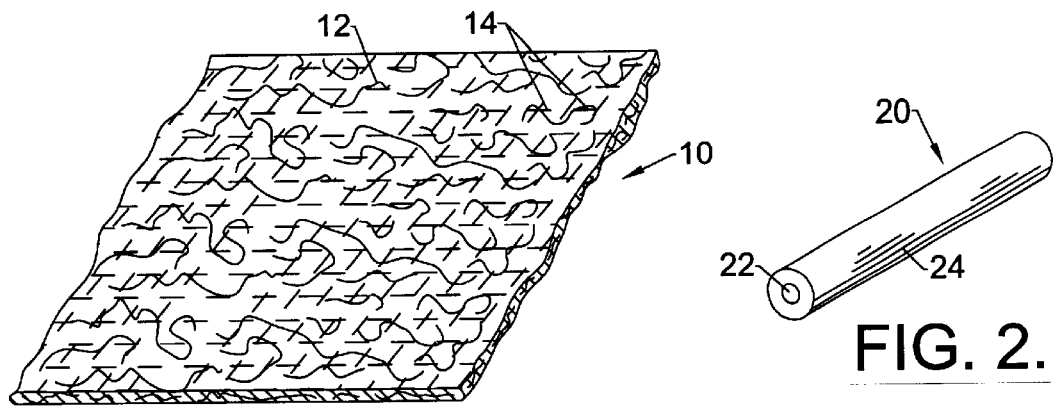
FIG. 1.
FIG. 2.
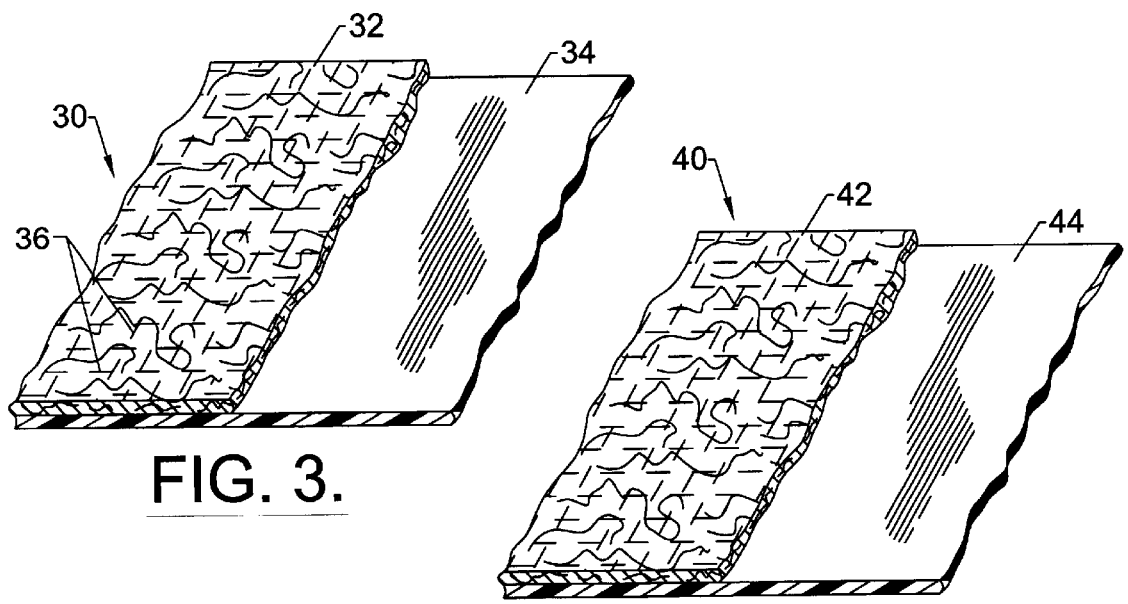
FIG. 3.
FIG. 4.
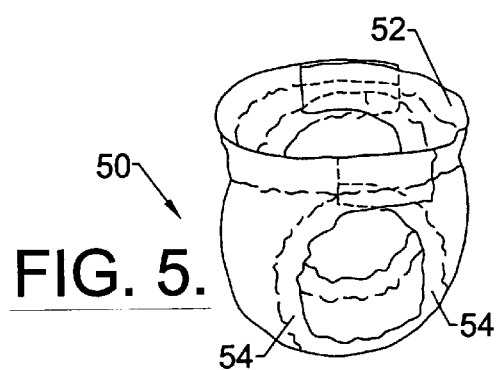
FIG. 5.

CENTER 45,000 X

MULTICOMPONENT FIBERS AND FABRICS MADE USING THE SAME

CROSS REFERENCE TO RELATED APPLICATIONS

This application is a continuation-in-part application of U.S. application Ser. No. 08/997,082, filed Dec. 23, 1997, now abandoned which is a continuation of U.S. application Ser. No. 08/676,360, filed Aug. 27, 1996, now U.S. Pat. No. 5,804,286 which is a continuation-in-part of each of U.S. application Ser. No. 08/344,419 now abandoned, Ser. No. 08/344,731 now abandoned, and Ser. No. 08/344,732, now U.S. Pat. No. 5,543,206, each of which was filed Nov. 23, 1994, the entire disclosure of each of which is hereby incorporated by reference.

FIELD OF THE INVENTION

The present invention relates to multicomponent fibers, as well as nonwoven fabrics and fabric laminates which comprise the multicomponent fibers. More particularly, the invention relates to multicomponent fibers which include at least one polymer domain formed of a select combination of polymers, as well as nonwoven fabrics and laminates having improved fabric properties and processing characteristics.

BACKGROUND OF THE INVENTION

Nonwoven fabrics produced from spun polymer materials are used in a variety of different applications. Among other uses, such nonwoven fabrics are employed as the cover sheet for disposable diapers or sanitary products. There is considerable interest in making disposable diapers more comfortable and better fitting to the baby. An important part of the diaper comfort is the softness or hardness of the nonwovens used to make the diaper, including the diaper topsheet, barrier leg cuffs, and in some advanced designs, the fabric laminated to the backsheet film. In addition, in some diaper designs, a high degree of fabric elongation is needed to cooperate with elastic components for achieving a soft comfortable fit.

One approach to improved diaper topsheet softness is to use linear low density polyethylene (LLDPE) as the resin instead of polypropylene for producing spunbonded diaper nonwoven fabrics. For example, Fowells U.S. Pat. No. 4,644,045 describes spunbonded nonwoven fabrics having excellent softness properties produced from linear low density polyethylene. However, the above-described softness of LLDPE spunbonded fabric has never been widely utilized because of the difficulty in achieving acceptable abrasion resistance in such products. The bonding of LLDPE filaments into a spunbonded web with acceptable abrasion resistance has proven to be very difficult. Acceptable fiber tie down is observed at a temperature just below the point that the filaments begin to melt and stick to the calender. This very narrow bonding window has made the production of LLDPE spunbond fabrics with acceptable abrasion resistance very difficult. Thus, the softness advantage offered by LLDPE spunbonded fabrics has not been successfully captured in the marketplace.

Conventional polypropylene, which has been widely used in producing nonwoven fabrics, provides adequate fuzz and abrasion resistance properties in the unstretched condition, but the elongation properties are unacceptable and therefore the fibers and/or fabrics fracture.

In Sabee, U.S. Pat. Nos. 4,153,664 and 4,223,063, it is disclosed that the softness and drapeability of composite nonwoven fabrics, formed for example from a meltblown or a spunbonded nonwoven fabric, can be improved by drawing or stretching the fabric. More particularly, according to Sabee, the composite nonwoven fabrics are processed by differentially drawing or stretching the web to form a quilted pattern of drawn and undrawn areas, providing a product with enhanced softness, texture and drapeability. However, while the stretching may improve some fabric physical properties, it can adversely affect other important properties, such as abrasion resistance, for example, leaving the fabric with an unsightly fuzzed surface. In addition, Sabee teaches the use of undrawn or underdrawn filaments in the use of this application. Undrawn or underdrawn filaments are typically higher in denier and therefore the fabrics tend to be stiff. In addition to softness, often the performance requirements of the product demand a composite nonwoven fabric having elasticity. In certain disposable diaper designs, for example, it is desired to impart elastic properties to the waist and/or to the leg cuff areas. One approach which has been taken to providing such elastic properties in a composite nonwoven fabric involves forming and stretching an elastic web, then bonding a gatherable web to the elastic web, and relaxing the composite. An obvious limitation of this approach is having to form the composite in the tensioned state. This requires additional equipment and control systems. Examples of this process are Mormon, U.S. Pat. No. 4,657,802, where it is disclosed that a composite nonwoven elastic is made by first stretching an elastic web, forming a fibrous nonwoven gatherable web onto the stretched elastic nonwoven, joining the two together to form a composite structure, then allowing the composite to relax. In Collier, et al., U.S. Pat. No. 5,169,706, it is disclosed that a composite elastic material having a low stress relaxation is formed between an elastic sheet and a gatherable layer. In Daponte, U.S. Pat. No. 4,863,779, a composite is disclosed which involves first tensioning the elastic elastic web to elongate it, bonding at least one gatherable web to the elastic web, and relaxing the composite immediately after bonding, so that the gatherable web is gathered between the bond points.

Another approach to imparting elastic properties to a composite nonwoven fabric is with a so-called "zero-strain" stretchable laminate. A "zero-strain" stretchable laminate refers to a fabric in which at least two layers of material, one elastic, the other substantially inelastic, are secured to one another along their coextensive surfaces while in a substantially untensioned state. The fabric is subsequently subjected to mechanical stretching. The inelastic layer typically fractures or extends, thus permanently elongating the inelastic layer and producing a composite fabric with elastic properties. This lamination and stretching process is advantageous in that utilizing elastic in an unstretched condition is easier and less expensive than stretched elastic used in traditional processing operations. However, one problem which has existed with presently available "zero-strain" stretchable laminates is surface abrasion. The mechanical stretching either fractures or disrupts the fibers within the substantially inelastic component of the "zero-strain" laminate, and as a result, the fibers detach and are susceptible to linting and pilling. In addition, such fracturing or detachment causes a noticeable loss in fabric strength.

There have been attempts to address the aforementioned problems of fiber tie down and fabric abrasion resistance. For example, attempts have been made to make the nonwoven fabric component of the composite with high elongation properties. Conventional polypropylene, as noted above, which has been widely used in producing nonwoven fabrics, provides adequate fuzz and abrasion resistance properties in the unstretched condition, but the elongation properties are unacceptable and therefore the fibers and/or fabrics fracture. Nonwoven webs formed from linear low density polyethylene (LLDPE) have been shown to have high elongation properties and also to possess excellent hand, softness and drape properties. However, as also noted above, such fabrics have not found wide commercial acceptance, since they fail to provide acceptable abrasion resistance.

SUMMARY OF THE INVENTION

The present invention overcomes these disadvantages and limitations and provides multicomponent fibers and nonwoven fabrics formed of the same having a superior combination of extensibility, tensile properties and abrasion resistance. The multicomponent fibers of the invention include at least two polymer components arranged in structured domains. At least one of the polymer components is formed of a select blend of specific grades of polyethylene and polypropylene which give improved fabric performance not heretofore recognized or described, such as high abrasion resistance, good tensile properties, excellent softness and the like. Furthermore, these blends have excellent melt spinning and processing properties which permit efficiently producing nonwoven fabrics at high productivity levels.

The present invention is based upon the discovery that blending a relatively small proportion of polypropylene of a select class with the polyethylene imparts greatly increased abrasion resistance to a nonwoven fabric formed from the polymer blend, without significant adverse effect on the fabric softness properties. It is believed that the polyethylene and the polypropylene form distinct phases in the filaments. The lower-melting polyethylene is present as a dominant continuous phase and the higher-melting polypropylene is dispersed in the dominant polyethylene phase.

The multicomponent fibers can be continuous filaments, staple fibers, or meltblown fibers. Advantageously, at least a portion of the outer surface of the multicomponent fiber includes a polymer domain formed of the polymer blend to impart desired elongation, softness and abrasion resistance properties to the fibers and in turn to fabrics formed of the fibers. In a preferred embodiment, the fibers are bicomponent fibers with the polymer components arranged in a sheath-core structured domain. In this aspect of the invention, the sheath is formed of the polymer blend to impart the desired properties to the fibers and in turn to fabric produced using the same.

The physical and rheological behavior of these blends is part of a phenomenon observed by applicants wherein a small amount of a higher modulus polymer reinforces a softer, lower-modulus polymer and gives the blend better spinning, bonding and strength characteristics than the individual constituents. The lower melting, relatively low modulus polyethylene provides desirable properties such as softness, elongation and drape; while the higher-melting, higher modulus polypropylene phase imparts one or more of the following properties to the dominant phase: improved ability to bond the web; improved filament tie-down (reduces fuzz); improved web properties- tensiles, and/or elongation and/or toughness; rheological characteristics which improve spinning performance and/or web formation (filament distribution).

According to one advantageous aspect of the present invention, the lower-melting continuous phase comprises a linear low density polyethylene polymer of a melt index of greater than 10 (ASTM D1238-89, 190° C.) and a density of less than 0.945 g/cc (ASTMD-792). At least one higher-melting noncontinuous phase comprises a polypropylene polymer with melt flow rate of greater than 20 g/10 min (ASTM D1238-89, 230° C.). In one of the preferred embodiments of the invention, the lower-melting continuous phase of the blend comprises a linear low density polyethylene having a density of 0.90–0.945 g/cc and a melt index of greater than 25 g/10 minutes. In another preferred embodiment, the lower-melting polymer phase comprises linear low density polyethylene as described above and the higher-melting polymer phase comprises an isotactic polypropylene with a melt flow rate greater than 30 g/10 minutes. In another embodiment of the invention, the lower-melting polymer phase comprises linear low density polyethylene with a melt index of 27 and the higher-melting polymer phase comprises an isotactic polypropylene with a melt flow rate of 35 g/10 minutes.

According to another aspect of the present invention, the lower-melting dominant continuous phase is blended with a higher-melting noncontinuous phase of propylene co- and/or ter-polymers. When propylene co- and/or ter-polymers are used as the higher-melting noncontinuous phase, the lower melting continuous phase may be comprised of one or more polyethylenes selected from the group consisting of low density polyethylene, high pressure long chain branched polyethylene, linear low density polyethylene, high density polyethylene and copolymers thereof.

The multicomponent fibers of the invention are highly elongatable and are useful in the production of coherent extensible nonwoven fabrics having desirable yet contradictory properties. Specifically, the fibers of the invention can be formed into fabric exhibiting good softness, abrasion resistance and elongation. According to one embodiment of the present invention, the coherent extensible nonwoven web is a thermally bonded spunbond nonwoven web of randomly arranged substantially multicomponent continuous filaments, in which at least one polymer domain is formed of multiple polymers. According to another embodiment of the invention, the coherent extensible nonwoven web is a thermally bonded carded web of multicomponent staple fibers. The coherent extensible nonwoven web may contain, in addition to the multicomponent fibers, additional fibrous components, such as meltblown microfibers. The fabrics of the present invention can have a Taber surface abrasion value (rubber wheel) of greater than 10 cycles and an elongation at peak load in at least one of the machine direction or the cross-machine direction of at least 70%.

In accordance with another embodiment of the invention, the nonwoven fabric may include one or more additional layers or components laminated thereto. Exemplary additional layers include continuous or perforated polymer films, films or webs of an elastic polymer, spunbonded nonwoven webs, extensible scrims or nets, an array of extensible or elastic strands, a web of meltblown microfibers, a web of staple fibers, and the like. Where an elastic web or film is used, the composite can be stretch activated by elongation, which causes permanent elongation and stretching of the coherent extensible web of multicomponent fibers, and the resulting composite fabric exhibits elastic properties. Where an extensible nonelastic layer is used, such as polyolefin film for example, the composite can be stretch activated by elongation, for example to at least 20% of its original unstretched length, producing a composite having excellent softness and drape.

The resultant composite fabrics can have a cloth like hand and good cover characteristics suitable for use in disposable absorbent garments, such as diapers, incontinence pads, sanitary napkins and the like. The composite fabrics are particularly useful as components of disposable diapers, such as in leg barrier cuffs, side panels, backsheet, topsheet, and the like.

BRIEF DESCRIPTION OF THE DRAWINGS

Some of the objects and advantages of the invention have been stated. Others will appear when taken in connection with the accompanying drawings, in which:

FIG. 1 is a schematic perspective view of a nonwoven fabric formed of multicomponent fibers of the invention;

FIG. 2 is a schematic perspective view of a multicomponent fiber of the invention;

FIG. 3 is a schematic perspective view of a nonwoven composite fabric which includes as a component a fabric formed of multicomponent fibers of the invention, with the respective layers being exposed for clarity of illustration;

FIG. 4 is a schematic perspective view of an alternative nonwoven composite fabric which includes as a component a fabric formed of multicomponent fibers of the invention;

FIG. 5 is a side view of a diaper incorporating the composite fabric of the invention as a component;

DETAILED DESCRIPTION OF THE PREFERRED EMBODIMENTS

Figure 6A:
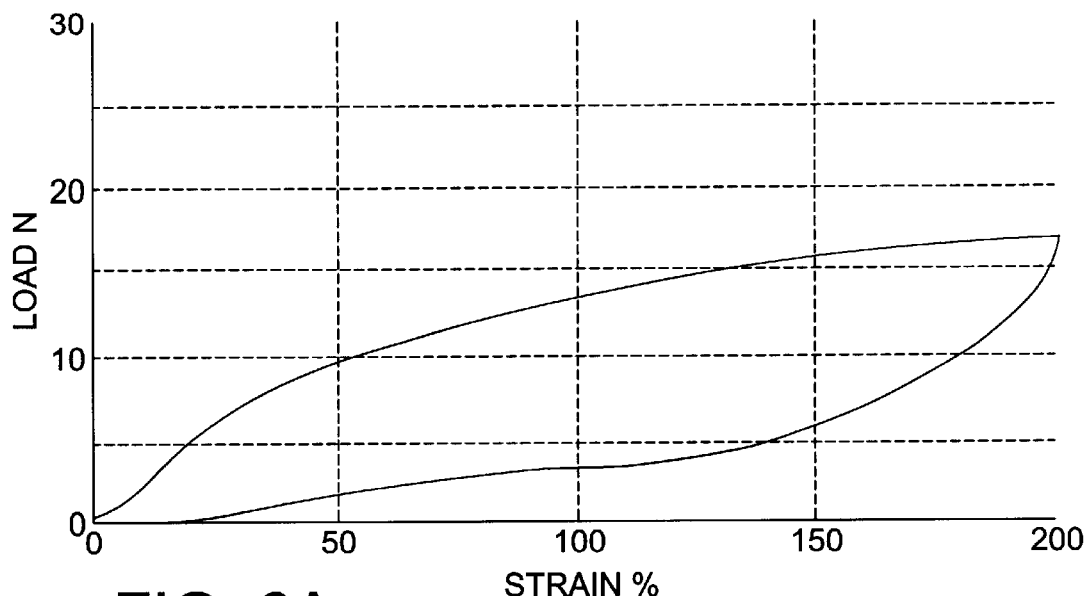
FIGS. 6A and 6B are graphs showing the stress-strain relationships of the fabric sample described in Example 11 after a first and second elongation, respectively.

The present invention will be described more fully hereinafter in connection with illustrative embodiments of the invention which are given so that the present disclosure will be thorough and complete and will fully convey the scope of the invention to those skilled in the art. However, it is to be understood that this invention may be embodied in many different forms and should not be construed as being limited to the specific embodiments described and illustrated herein. Although specific terms are used in the following description, these terms are merely for purposes of illustration and are not intended to define or limit the scope of the invention.

FIG. 1 is a schematic perspective view of a nonwoven fabric, designated generally as 10, formed of multicomponent fibers 12 of the invention. The nonwoven fibrous web represented in FIG. 1 should be considered in a generic sense to include generally planar structures that are relatively flat, flexible and porous and are comprised of multicomponent staple fibers or continuous filaments. The nonwoven web may be made by any of a number of manufacturing techniques well known in the nonwovens field, such as but not limited to carding, spunbonding, wet laying, air laying, meltblowing, and the like.

For example, in the embodiment illustrated in FIG. 1, the nonwoven fibrous web is a spunbonded nonwoven comprising bicomponent spunbond continuous filaments. The spunbonded web may be produced by the conventional spunbond process wherein molten polymer is extruded into continuous filaments which are subsequently quenched, attenuated by a high velocity fluid and collected in random arrangement on a collecting surface. After filament collection, any thermal, chemical or mechanical bonding treatment may be used to form a bonded web such that a coherent web structure results.

In the embodiment shown in FIG. 1, web 10 is bonded by a plurality of intermittent bonds, indicated generally as 14, distributed throughout the fabric to form a unitary, coherent nonwoven web. In this regard, thermal point bonding is most preferred. Various thermal point bonding techniques are known, with the most preferred utilizing calender rolls with a point bonding pattern. Any pattern known in the art may be used with typical embodiments employing continuous or discontinuous patterns. Preferably the bonds 14 cover between 6 and 30 percent of the area of the web 10, more preferably 8 to 20 percent and most preferably 12 to 18 percent. By bonding the web in accordance with these percentage ranges, the filaments are allowed to elongate throughout the full extent of stretching while maintaining the strength and integrity of the fabric.

Alternatively, the extensible coherent nonwoven web 10 can be a carded nonwoven web of staple fibers. As known, carding is typically carried out on a machine which utilizes opposed moving beds or surfaces of fine, angled, spaced apart teeth or wires to pull clumps of staple fibers into a web. Fibers within the web are then subjected to bonding to form a coherent web structure by any suitable thermal, chemical or mechanical bonding treatment. For example, thermal point bonds are formed in a manner previously described to impart strength and flexibility to the fabric.

Turning to FIG. 2, a schematic perspective view of an exemplary multicomponent fiber 20 of the invention is illustrated. As illustrated in FIG. 2, in a preferred embodiment of the invention, the fibers are bicomponent fibers having an inner core polymer domain 22 and surrounding sheath polymer domain 24. As used herein, the term "multicomponent fibers" includes staple and continuous filaments prepared from two or more polymers present in discrete structured domains in the fiber, as opposed to blends where the domains tend to be dispersed, random or unstructured. For purposes of illustration only, the present invention will generally be described in terms of a bicomponent fiber comprising two components. However, it should be understood that the scope of the present invention is meant to include fibers with two or more structured components.

In general, the polymer domains or components are arranged in substantially constantly positioned distinct zones across the cross section of the multicomponent fiber and extend continuously along the length of the multicomponent fiber. A preferred configuration is a sheath/core arrangement, wherein a first component, the sheath, substantially surrounds a second component, the core. The weight ratio of polymer domains or components can vary. Typically, the weight ratio of the first polymeric component to the second polymeric component ranges from about 20:80 to about 80:20, although the weight ratio can be outside of this range as well.

The polymer blends of the invention are particularly advantageous in the production of engineered fabrics. In this regard, the weight ratios of the polymeric components can be readily varied to impart desired properties to the fibers and fabrics produced therefrom. For example, aesthetic properties such as softness and hand, elongation, and the like can be optimized in a given fabric construction by increasing and/or maximizing the weight ratio of a polymer component imparting this property. For example, the multicomponent fiber can include a relatively high weight ratio of polymeric component(s) formed of the low melt polymer dominant blends described below or even single polymer components of elongatable polymers such as polyethylene. The weight ratios can be increased up to 60%, 80% and higher. Alternatively, to maximize tenacity or strength, the fibers can be engineered so as to maximize the weight ratio of a high melt polymeric component, for example high melt polymer dominant blends described below, as well as single polymer components such as a polyethylene terephthalate core in a sheath/core fiber. A balance of properties can be achieved, for example, with substantially equal ratios of components (for example an approximately 50/50 sheath/ core fiber structure). Other structured fiber configurations as known in the art may be used, such as but not limited to, side-by-side, segmented pie, islands-in-the-sea, or tipped multilobal structures.

The cross section of the multicomponent fiber is preferably circular, since the equipment typically used in the production of multicomponent synthetic fibers normally produces fibers with a substantially circular cross section. The configuration of the first and second components in a fiber of circular cross section can be either concentric or acentric, the latter configuration sometimes being known as a "modified side-by-side" or an "eccentric" multicomponent fiber.

The concentric configuration is characterized by the first component having a substantially uniform thickness, such that the second component lies approximately in the center of the fiber. In the acentric configuration, the thickness of the first component varies, and the second component therefore does not lie in the center of the fiber. In either case, the second component is substantially surrounded by the first component. However, in an acentric bicomponent fiber, a portion of the second component may be exposed, such that in practice up to about 20% of the surface of the fiber may be comprised of the second component. The first component in a fiber with an acentric configuration will nevertheless comprise the major part of the surface of the fiber, i.e., at least about 80%. Both the cross section of the fiber and the configuration of the components will depend upon the equipment which is used in the preparation of the fiber, the process conditions and the melt viscosities of the two components.

In the invention, at least one polymer domain is formed of a polymer blend, as described in more detail below. Other of the polymer domains of the fibers of the invention can be formed of a single polymer or of a polymer blend, including but not limited to any of the polymer blends described below. Advantageously, at least one polymer domain or component comprising the polymer blend forms an exposed surface on at least a portion of the fiber. For example, a preferred embodiment of the invention is a sheath/core bicomponent fiber in which the sheath is formed of a polymer blend. However, other of the polymer domains can also be formed of a polymer blend (for example, the core and/or both the sheath and core).

The multipolymer blend component of the multicomponent fibers of the invention is predominantly formed from polymers that normally are considered nonelastic. Useful polymer combinations for use in the practice of the invention are taught in published PCT International Patent Application PCT/US95/15257, filed Nov. 22, 1995, and entitled Extensible Composite Nonwoven Fabrics now WO 96/16216. The contents of this application and the teachings contained therein are hereby incorporated by reference in their entirety.

As discussed herein, fibers and fabrics formed of the multipolymer blend fibers of the invention can have good elongation or extensibility properties. In this regard, fabrics of the invention can exhibit an elongation ratio of elongation of the fabric of the invention relative to the elongation of a comparable fabric formed of 100% polypropylene fibrous material of at least about 1, preferably at least about 1.2, more preferably at least about 1.5, and most preferably at least about 2 and higher. Although not wishing to be bound by any explanation of the invention, it is currently believed that the domain size of the dispersed polymer for polyethylene dominant blends can impact the physical properties of the fabric, as demonstrated by the examples of the present application. See Tables 1 and 2 of the present application which report CD and MD elongation values of fabrics formed of polymer blends, in comparison with CD and MD elongation values of 100% polyethylene and polypropylene controls.

Certain three component polymer blends of the invention, as described in more detail below, are particularly advantageous in this regard. Fabrics formed of such blends can not only provide improved extensibility as compared to comparable 100% polypropylene fabrics, but also fabrics formed of two-component polymer blends, and in particular blends of polypropylene homopolymers and Catalloy polypropylene copolymers. Studies have shown that fabrics formed of polypropylene/Catalloy blend filaments exhibit elongation value similar to that of 100% polypropylene fabrics (typically about 70 to 80% in the cross machine direction). The three polymer formulations can provide greatly improved elongation of at least about 150% in the cross machine direction.

For the purposes of the invention, the term "polymer" is used in a general sense, and is intended to include homopolymers, copolymers, grafted copolymers, and terpolymers. The term blend is also used generally herein, and is intended to include immiscible and miscible polymer blends. The polymers are considered to be "immiscible" if they exist in separate, distinct phases in the molten state; all other blends are considered to be "miscible." It is understood that varying levels of miscibility can exist, and are also intended to be within the scope of this invention. The multipolymer fibers are normally formed of a polymer blend composed of two or more polymers, although blends with more than two polymers may also be utilized, including those with three or more polymer components. Both immiscible and miscible polymers may be added to a two component blend to impart additional properties or benefits with respect to blend compatibility, viscosity, polymer crystallinity or phase domain size.

Since the polymers employed in the invention will undergo extrusion, stabilizers and antioxidants are conventionally added to the polymer. Other additives may also be added in accordance with the present invention. For example inorganic additives such as titanium dioxide, talc, fumed silica or carbon black. The polymer resin may also contain other additives, such as other polymers, diluents, compatibilizers, antiblocking agents, impact modifiers, plasticizers, UV stabilizers, pigments, delusterants, lubricants, wetting agents, antistatic agents, nucleating agents, rheology modifiers, water and alcohol repellents, and the like. It is also anticipated that additive materials which have an affect on processing or product properties, such as extrusion, quenching, drawing, laydown, static and/or electrical properties, bonding, wetting properties or repellency properties may also be used in combination with the blend. In particular, polymeric additives may also be used that impart specific benefits to either processing and/or end use.

According to one broad aspect of the invention, at least one polymer domain of the multicomponent fibers includes at least one polymer domain formed of a polymer blend composed of two or more polymers. The polymers of the blend can be miscible, immiscible, or a combination of miscible and immiscible polymers. In one embodiment in accordance with the invention, the polymers may exist as a dominant continuous phase and at least one substantially discontinuous dispersed phase. In the case where the blend exists as a dominant continuous phase and at least one discontinuous phase, other polymers may also be present which are either miscible in one, or the other, or both polymer phases.

According to a further aspect of the invention, at least one polymer domain of the multipolymer fibers is formed of a polymer blend including a relatively low modulus polymer and at least one higher modulus polymer. It is believed that this combination is particularly valuable when the low modulus polymer is the dominant phase and the higher modulus polymer is dispersed therein. It is theorized that the higher modulus polymer acts to 'reinforce' the low modulus dominant phase, lending stability to spinning, and stiffening the web just enough to allow for higher bond temperatures while reducing the risk of the web sticking to and wrapping the calender. In the case of multicomponent fibers having at least one polymer domain formed of an immiscible polymer blend it is believed that the small amount of the dispersed polymer may have the effect of wind up speed suppression (WUSS) on the dominant polymer phase as described by Brody in U.S. Pat. No. 4,518,744. Wind up speed suppression occurs when a small amount of an immiscible additive effectively reduces the degree of molecular orientation within the fiber at a given filament spinning velocity. The result is a filament with generally higher elongation and lower tenacity.

In yet another aspect of the invention, at least one polymer domain of the multipolymer fibers is formed of a polymer blend composed of a dominant continuous phase, and at least one polymer, having low mutual affinity with the dominant phase, dispersed therein, and at least one additional polymer which is at least partially miscible in one or the other or both continuous and dispersed polymer phases. If the one additional polymer is miscible in the dominant phase, and effectively reduces its crystallinity, it is believed that the improved extensibility observed in the resulting composites may be due to an 'impact-modifying' effect. If the one additional polymer has an affinity for both polymers, or serves to lower the surface energies between the two phases, it is believed that the improvement observed in the composite extensibility is due to a compatibilization effect. Independent of theory, the blend must ultimately form filaments or fibers, which when formed into webs and composite structures exhibit the properties described by the invention, meaning low fuzz and good elongation.

In one embodiment, at least one polymer domain of the multicomponent fibers may comprise from 1 to 50 percent by weight polyethylene and from 99 to 50 percent by weight polypropylene. Fabrics formed from such fibers exhibit low fuzz and good elongation.

In applications where tensile strength is particularly important and high elasticity is of lesser concern, the composite fabric may include a coherent, extensible nonwoven web formed of multicomponent fibers having at least one polymer domain formed of a polyethylene and polypropylene blend where the polyethylene is present in the range of 1% to 10% and the polypropylene is present in the range of 90% to 99% by weight. In still another embodiment, very substantial and surprising increases in elongation can be achieved by blending a third polymer component into the blend. For example, the multicomponent fibers may include at least one polymer domain comprising a dominant amount of a polypropylene, such as isotactic polypropylene, a small amount of a polymer having low mutual affinity with the dominant polymer, such as polyethylene, and an additional third polymer which either reduces crystallinity and/or compatibilizes the blend. What results is a softer web, with extremely high extensibility. Preferred multicomponent fibers according to this embodiment may have at least one polymer domain comprising greater than 50 percent by weight polypropylene, 1 to 10 percent polyethylene, and 10 to 40 percent of the third polymer. Suitable additional third polymers include polypropylene copolymers and terpolymers such as the commercially available Catalloy® copolymers available from Montell. These resins are characterized by having the comonomer(s) exist to some degree in blocks, and wherein at least some portion of the polymer chain is miscible with one or the other, or both, dominant and dispersed polymer phases. Other suitable polymers are the Reflex® flexible polyolefins from Rexene. These crystallinity reducing resins are characterized as having atactic segments present in the polymer chain, such that the "tacticity" of the polymer is affected. Especially preferred multicomponent fibers according to this embodiment comprise at least one polymer domain comprising 65 to 80 percent isotactic polypropylene, 1 to 5 percent polyethylene, and 15 to 30 percent of a polyolefin copolymer wherein at least a portion of the chain is miscible with isotactic polypropylene.

As noted above, three component blends of the invention can provide particularly advantageous extensibility or elongation properties. Although not wishing to be bound by any theory of the invention, it is believed that incorporating a minor component of the Catalloy polypropylene copolymer or other such polymer imparts sufficient "give" to the polypropylene majority component so that the fabric can resist breaking until the more elongatable component, polyethylene, is activated to provide the increased elongation values. In addition, it is believed that fabrics formed of certain three polymer blend formulations can be bonded at lower temperatures due to a lowered or decreased melting point, as compared to 100% polypropylene fabrics and other polypropylene blend fabrics. For example, fabrics prepared using the formulations noted above which include a Catalloy polymer minor component can be thermally bonded at temperatures of about 20° C. less than that typically required for fabrics formed of 100% polypropylene filaments or polypropylene/polyethylene blend filaments.

Still further, certain three polymer component blends (and in particular those including a Catalloy minor polymer component) can exhibit elastic properties as defined in U.S. Pat. No. 5,470,639 to Gessner et al. The '639 patent defines elastic spunbonded fabrics as having a root mean square (RMS) recoverable elongation of at least about 75% in both the machine direction (MD) and the cross direction (CD) after 30% elongation and one pull, and preferably at least about 70% after two pulls. Spunbonded fabrics formed of the above three polymer component formulation can meet the criteria for elasticity as defined by the Gessner '639 patent.

Another class of useful and advantageous products according to this aspect of the invention employ multicomponent fibers having at least one polymer domain formed of a polymer blend comprised of a soft, extensible polymer phase, and at least one additional polymer having low mutual affinity with the soft, extensible phase, such that it modifies either the rheological, mechanical, and/or thermal properties of the fibers in a way that improves processability (e.g. melt spinning), bonding and/or abrasion resistance while maintaining high extensibility. In a preferred embodiment the soft, extensible phase is present as a dominant, continuous phase. For example, polyethylene can be used as the soft, extensible dominant phase and a polypropylene as the additional modifying polymer. In a preferred embodiment the additional polymer is added in a small proportion relative to the dominant phase. In another preferred embodiment, the additional polymer exhibits higher viscosity relative to the dominant phase. Blending a relatively small proportion of the higher viscosity polypropylene with the soft, extensible polyethylene imparts greatly increased abrasion resistance to a nonwoven fabric formed from the polymer blend, without significant adverse effect upon other important fabric properties, such as extensibility, softness, tensile strength, etc. The spinnability of the polyethylene is also improved by the presence of the additional polypropylene. According to this embodiment, at least one polymer domain of the multicomponent fibers preferably comprises between 2 to 50 percent by weight of the propylene polymer, e.g. 3% ethylene-propylene copolymer, and 98 to 50 percent by weight of the soft, extensible polymer, e.g. polyethylene. In one particularly preferred embodiment, at least one polymer domain of the multicomponent fiber may range from 5 to 40 percent by weight propylene polymer, and most desirably between 5 to 25 percent by weight propylene polymer and 75 to 95 percent by weight polyethylene. Especially suited for applications requiring good extensibility, tensile strength and abrasion resistance are multicomponent fibers having at least one polymer domain comprising compositions of from 5 to 25 percent by weight propylene polymer. A most preferred embodiment contains 5 to 25 percent by weight of ethylene-propylene copolymer or terpolymer and 75 to 95 percent by weight linear low density polyethylene. In these embodiments, the lower melting polyethylene is present as a substantially continuous phase in the blend and the higher melting propylene polymer is present as a discontinuous phase dispersed in the polyethylene phase.

The other structured polymer domains of the multicomponent fibers of the invention can be formed of any of the various well known filament forming polymers, such as but not limited to polyolefins, such as polypropylene, polyethylene, and the like; polyamides; polyesters; and the like, as well as co- and terpolymers and blends thereof. As noted above, in one aspect of the invention, the multicomponent fibers include along at least an outer portion of the surface thereof a polymer domain formed of a polyethylene dominant blend (for example, as a sheath component). Such a fiber configuration is particularly desirable in combination with a polypropylene polymer domain (for example, as a core component). These fibers can exhibit desirable yet contradictory properties of softness and abrasion resistance. In another embodiment of the invention, the fibers include a polymer domain formed of a propylene dominant blend as described above (for example, as a core component). Useful fibers in this embodiment include those having a propylene dominant domain in combination with a polyethylene component extending along at least a portion of the surface of the fiber (for example, as the sheath). These fibers can also exhibit desirable yet contradictory properties, such as desirable hand with good elongation. In yet another embodiment of the invention, the fibers include along at least an outer portion of the surface thereof a polymer domain formed of a polyethylene dominant blend and a polymer domain formed of a propylene dominant blend, for example a sheath core fiber structure in which the sheath is formed of a polyethylene dominant blend and the core is formed of a propylene dominant blend.

In producing the fibers, polymer blend components (i.e., the polyethylene and polypropylene components) are combined in appropriate proportional amounts and intimately blended before being melt-spun. In some cases sufficient mixing of the polymer components may be achieved in the extruder as the polymers are converted to the molten state. In other cases, more dynamic mixing may be required. Among the commercially available mixers that can be used are the Barmag 3DD three-dimensional dynamic mixer supplied by Barmag AG of West Germany and the RAPRA CTM cavity-transfer mixer supplied by the Rubber and Plastics Research Association of Great Britain.

The polymer blend can be extruded to produce a multi-component fiber structure using suitable equipment and processing techniques as known in the art for the production of multicomponent fibers. For example, the polymer components may be fed into two extruders to melt extrude the polymers. The polymer melts are then directed into a spinneret with composite spinning orifices of sheath/core, side-by-side or other multicomponent fiber types and spun through this spinneret to form the multicomponent fibers. See, for example, U.S. Pat. Nos. 3,595,731 and 4,770,925.

Various types of polyethylene may be employed. As an example, a branched (i.e., non-linear) low density polyethylene or a linear low density polyethylene (LLDPE) can be utilized and produced from any of the well known processes, including metallocene and Ziegler-Natta catalyst systems. LLDPE is typically produced by a catalytic solution or fluid bed process under conditions established in the art. The resulting polymers are characterized by an essentially linear backbone. Density is controlled by the level of comonomer incorporated into the otherwise linear polymer backbone. Various alpha-olefins are typically copolymerized with ethylene in producing LLDPE. The alpha-olefins which preferably have four to eight carbon atoms, are present in the polymer in an amount up to about 10 percent by weight. The most typical comonomers are butene, hexene, 4-methyl-1-pentene, and octene. In general, LLDPE can be produced such that various density and melt index properties are obtained which make the polymer well suited for melt-spinning with polypropylene. In particular, preferred density values range from 0.87 to 0.95 g/cc (ASTM D-792) and melt index values usually range from 0.1 to about 150 g/10 min. (ASTM D1238-89, 190° C.). Preferably, the LLDPE should have a melt index of greater than 10, and more preferably 15 or greater for spunbonded filaments. Particularly preferred are LLDPE polymers having a density of 0.90 to 0.945 g/cc and a melt index of greater than 25. Examples of suitable commercially available linear low density polyethylene polymers include those available from Dow Chemical Company, such as ASPUN Type 6811 (27 MI, density 0.923), Dow LLDPE 2500 (55 MI, 0.923 density), Dow LLDPE Type 6808A (36 MI, 0.940 density), and the Exact series of linear low density polyethylene polymers from Exxon Chemical Company, such as Exact 2003 (31 MI, density 0.921).

Various polypropylenes made by processes known to the skilled artisan may also be employed. In general, the polypropylene component can be an isotactic or syndiotactic propylene homopolymer, copolymer, or terpolymer. Examples of commercially available propylene homopolymers which can be used in the present invention include SOLTEX Type 3907 (35 MFR, CR grade), HIMONT Grade X10054-12-1 (65 MFR), Exxon Type 3445 (35 MFR), Exxon Type 3635 (35 MFR) AMOCO Type 10-7956F (35

MFR), and Aristech CP 350 J (melt flow rate approximately 35). Examples of commercially available copolymers of propylene include Exxon 9355 which is a random propylene copolymer with 3% ethylene, 35 melt flow rate; Rexene 13S10A, a 10 melt flow rate random propylene copolymer with 3% ethylene; Fina 7525MZ, an 11 melt flow rate 3% ethylene random propylene copolymer; Montel EPIX 30F, a 1.7% ethylene, 8 melt flow rate random copolymer of propylene and co- and ter-polymers of propylene from the Catalloy™ series from Himont. When the polypropylene polymer exists as the dispersed phase of the blend, the preferred melt flow should be greater than 20 g/10 min., and preferably 25 or greater. Particularly suitable are polypropylene polymers having an MFR of 35 to 65.

When the lower-melting polyethylene component is present as a substantially continuous phase and the higher-melting polypropylene is present as a discontinuous phase dispersed in the polyethylene phase, the lower-melting polyethylene component and the higher-melting polypropylene component can be present in proportions ranging from about 50 to about 99 percent by weight polyethylene and about 50 to about 1 percent polypropylene, more preferably from about 50 to about 98 percent by weight polyethylene and about 50 to about 2 percent polypropylene, more preferably from about 60 to about 95 percent by weight polyethylene and about 40 to about 5 percent polypropylene, and most preferably from about 75 to about 95 percent by weight polyethylene and about 25 to about 5 percent polypropylene.

The polymer constituents of the structured polymer domains can be selected so as to impart other desirable characteristics to the fabric, such as high surface abrasion resistance and high elongation. The surface abrasion resistance of the web may be conveniently measured objectively by physical tests which are standard in the industry, such as the Taber abrasion test as defined by ASTM Test Method D-3884-80. Extensible webs useful in the composite fabrics of the present invention are characterized by having a Taber abrasion value (rubber wheel) of greater than 10 cycles. The webs are further characterized by having an elongation at peak load (ASTM D-1682), prior to stretching, in either the machine direction (MD) or in the cross-machine direction (CD) or both of at least 70 percent, more preferably at least 100 percent, and most desirably at least 150 percent. Thus the fabrics can generally be characterized as "extensible noneleastic" fabric, meaning that the web 10 can be relatively easily stretched beyond its elastic limit and permanently elongated by application of tensile stress. However, the web has little retractive force and therefore is noneleastic.

Turning now to FIG. 3, a perspective view of an exemplary laminate fabric of the invention, designated generally as 30, is illustrated. In this embodiment, laminate 30 is a two-ply laminate. Ply 32 comprises a nonwoven web formed of multicomponent fibers, such as fabric 10 as described above. The second layer 34 of the composite fabric 30 can exist in various forms, such as but not limited to a meltblown nonwoven web, a spunbonded web, a web of staple fibers, or a film. Although FIG. 3 illustrates a two-ply laminate, the skilled artisan will appreciate that additional plies, which can be the same or different from the plies 32 and 34, can also be present.

The plies may be bonded and/or laminated in any of the ways known in the art. Lamination and/or bonding may be achieved, for example, by hydroentanglement of the fibers, spot bonding, through-air bonding and the like. For example, when ply 34 is a fibrous web, lamination and/or bonding may be achieved by hydroentangling, spot bonding, through-air bonding and the like. In the embodiment shown in FIG. 3, plies 32 and 34 are laminated together by passing through a heated patterned calender to form discrete thermal point bonds indicated at 36. It is also possible to achieve bonding through the use of an appropriate bonding agent, i.e., an adhesive. The term spot bonding is inclusive of continuous or discontinuous pattern bonding, uniform or random point bonding or a combination thereof, all as are well known in the art.

The bonding may be made after assembly of the laminate so as to join all of the plies or it may be used to join only selected of the fabric plies prior to the final assembly of the laminate. Various plies can be bonded by different bonding agents in different bonding patterns. Overall, laminate bonding can also be used in conjunction with individual layer bonding.

Laminates of a spunbond web from the multicomponent fibers as described above with a web of meltblown microfibers have utility as barrier fabrics in medical applications, protective clothing applications, and for hygiene applications such as barrier leg cuffs. Of particular utility for hygiene applications are spunbond/meltblown laminates of reduced basis weight, such as made with a 17 grams per square meter (gsm) spunbonded web of this invention and 2–3 gsm meltblown web. Such barrier laminates could be used, for example, as barrier leg cuffs in diapers.

Another type of nonwoven fabric laminate may be made by combining nonwoven webs of this invention with a film, for example a film of a thermoplastic polymer, such as a polyolefin, to make barrier fabrics useful for hygiene applications such as barrier leg cuffs and diaper backsheets. FIG. 4 illustrates one such laminate 40, which includes a ply or layer 42 comprising a nonwoven web formed of the multicomponent fibers of the invention, such as the nonwoven fabric 10 of FIG. 1, laminated to a polyolefin film layer 44, such as for example a polyethylene film of a thickness of 0.8 to 1 mil.

Useful films include both non-breathable and breathable films as known in the art. As used here, the term "breathable films" refers to films that provide a barrier to the passage of liquid (such as water, blood, urine, etc.) yet allow the passage of water as a vapor or in its gaseous state. Breathable films include films rendered breathable during the manufacture thereof (for example, by adding particulate material such as calcium carbonate to the melt during production of the film). Such films are commercially available. Breathable films also include films rendered breathable after manufacture. For example, breathability can be imparted to a film after lamination of the film to another substrate (such as the nonwoven fabrics of this invention) and stretching or elongating the laminate. Such fabric laminates are particularly useful as backsheet components in disposable absorbent articles including disposable diapers, medical fabrics, such as disposable medical or surgical gowns, and other protective clothing. See U.S. Pat. No. 5,865,926, to Wu et al. for a discussion of breathable films and methods of making the same.

Lamination and/or bonding of the nonwoven layer 42 to the film layer 44 can be achieved by adhesive lamination using a continuous or discontinuous layer of adhesive. This adhesive approach may yield a diaper backsheet with superior softness and hand. A suitable adhesive, if desired, is applied either to web 42, to web 44, or to both, as either a continuous or discontinuous coating. Where a continuous adhesive coating is employed, the adhesive layer should be relatively thin and the adhesive should be sufficiently flexible or extensible to allow the filaments to elongate upon stretching. Where a discontinuous adhesive is employed, any intermittent pattern can be used such as, for example, lines, spirals, or spots, and the adhesive can be less extensible. The adhesive can be applied continuously or intermittently by any accepted method including spraying, slot coating, meltblowing and the like.

Suitable adhesives can be made from a variety of materials including polyolefins, polyvinyl acetate polyamides, hydrocarbon resins, waxes, natural asphalts, styrenic rubbers, and blends thereof. Preferred adhesives include those manufactured by Century Adhesives, Inc. of Columbus, Ohio and marketed as Century 5227 and by H. B. Fuller Company of St. Paul, Minn. and marketed as HL-1258.

The nonwoven fabric laminate could also be produced by thermal lamination of the nonwoven fabric of this invention and film webs together. This approach has the advantage of eliminating the cost of the adhesive. It may also be desirable to utilize coextruded film webs that include a sealing/bonding layer in combination with a polyolefin layer in the film web that, when combined with the nonwoven fabrics of the invention, maximize softness and good thermal bonding characteristics. The nonwoven fabric laminate could also be produced by direct extrusion of the film layer 44 on ply 42.

Layer 44 is preferably a polyolefin film, most preferably a nonelastic polyolefin film that is extensible at least 100 percent of its original length. The film preferably has a basis weight within the range of 10 to 40 grams per square meter. The present invention is particularly applicable to extensible film/fabric composites where the film of the type conventionally used as the impermeable outer component of a disposable diaper.

Layers 34 or 44 of composite fabrics 30 and 40, respectively, can also be an elastic layer of various forms including webs of bonded filaments, nets, films, foams, parallel arrays of filaments, and the like. Such structures are produced by conventional methods known to the skilled artisan. For purposes of the present invention, an "elastic" layer is defined as having a 75% recovery after a single extension of 10% of the original dimension. As also known, any suitable elastomeric forming resins or blends thereof may be utilized in producing the above structures. Such suitable materials include the diblock and triblock copolymers based on polystyrene (S) and unsaturated or fully hydrogenated rubber blocks. The rubber blocks can consist of butadiene (B), isoprene (I), or the hydrogenated version, ethylene-butylene (EB). Thus, S-B, S-I, S-EB, as well as S-B-S, S-I-S, and S-EB-S block copolymers can be used. Preferred elastomers of this type include the KRATON polymers sold by Shell Chemical Company or the VECTOR polymers sold by DEXCO. Other elastomeric thermoplastic polymers include polyurethane elastomeric materials such as ESTANE sold by B. F. Goodrich Company; polyester elastomers such as HYTREL sold by E. I. Du Pont De Nemours Company; polyetherester elastomeric materials such as ARNITEL sold by Akzo Plastics; and polyetheramide materials such as PEBAX sold by Elf Atochem Company; polyolefin elastomers such as Insite™, Affinity™ or Engage™ polyethylene plastomers from Dow Chemical or the Exact™ polyethylene plastomers available from Exxon Chemical. Crosslinked elastomers such as crosslinked urethanes and rubbers may also be employed. Blends of these polymers with other polymers, such as, for example, polyolefins may be employed to enhance processing such as decreasing melt viscosity, allowing for lower melt pressures and temperatures and/or increase throughput.

In one aspect of the invention, in assembling the composite fabric 40, layers 42 and 44 are provided in an unstretched state from individual supply rolls. If desired, adhesive is then applied over the surface of extensible web 42 or layer 44. Soon after the adhesive is applied, the layers are subjected to pressure thus forming fabric 40. For example, the layers can be fed through calender nip rolls. Alternatively, the fabric can be bonded by thermal means with or without an adhesive.

In a further embodiment, the composite fabrics 30 or 40 of FIGS. 3 and 4, respectively, include an additional component on the side of extensible web 32 or 42 opposite layer 34 or 44 to form a trilaminate. This third component may or may not be extensible. Any suitable material may be employed in various forms such as, for example, woven or nonwoven material, films or composites, such as a film-coated nonwoven. For example, a thermoplastic polymer film can be used, with preferred polymers being polypropylene or polyethylene. Commercially desirable films includes those manufactured by Tredegar Industries, Inc. of Terre Haute, Ind. If the component is substantially impervious to liquids, it can be suitably employed as a back sheet in personal garment applications such as diapers, training pants, incontinence briefs and feminine hygiene products. Any well known techniques for laminating component to the composite structure may be utilized; preferably, component is laminated by a thin layer of adhesive in a manner previously described.

Alternatively, the additional component can be a nonwoven web, which can be constructed to be extensible or essentially nonextensible. For example, the nonwoven web may be another web of multicomponent fibers similar to web 32 or 42 so that a fibrous web is used on both faces of the composite fabric 30 or 40. An essentially nonextensible nonwoven web can also be employed, such as a carded thermally point bonded web of low elongation fibers such as Hercules Type 196 polypropylene staple fibers.

Stretching forces can be applied to composite fabric 30 or 40 to extend and elongate the fabric in the machine direction (MD) and/or cross-machine direction (CD). Numerous established techniques can be employed in carrying out this operation. For example, a common way for obtaining MD elongation is to pass the fabric through two or more sets of nip rolls, each set moving faster than the previous set. CD elongation may be achieved through tentering. Other means may be employed; for example, "ring rolling" as disclosed in U.S. Pat. No. 5,242,436 to Weil et al., incorporated herein by reference, is often used in obtaining CD and/or MD elongation.

Upon application of elongation forces on fabric 30 or 40, fibers within extensible layer 32 or 42 oriented in the direction of the elongation experience tension and the fabric and fibers undergo deformation. During this process, the fibers are capable of elongating well beyond their unstretched length. As an example, fabric elongation between 70 and 300 percent is often realized. In most instances, the fibers are elongated past their elastic limit, undergo plastic deformation, and become permanently extended. In accordance with the invention, intermittent bonds distributed throughout nonelastic layer 32 or 42 are of high strength such that fibers are sufficiently tied down within the nonelastic layer 32 or 42 and fiber detachment is minimized during the elongation process. Accordingly, fiber detachment is reduced with the desirable result that abrasion resistance is maintained and fizzing is minimized. Moreover, fabric strength is maintained as the coherent web structure is kept intact during the elongation operation.

The composite fabrics of the invention are particularly well suited for use in various disposable garments such as diapers, training pants, incontinence briefs and feminine hygiene products. The fabric may be utilized in a diaper, such as the one illustrated in FIG. 5 (denoted as 50) having a waist region 52 and leg cuff components 54. Since the composite fabric is both soft and strong, the diaper can withstand rigorous movement of the wearer without rubbing or chafing the wearer's skin during use.

The following examples serve to illustrate the invention but are not intended to be limitations thereon.

EXAMPLE 1

This example illustrates the benefits of fibers formed using various multipolymer systems in producing low fuzz, highly extensible spunbond nonwoven fabrics, and compares the fabric properties to a conventional spunbond fabric made of 100 percent isotactic polypropylene. Continuous filament spunbond nonwoven fabrics were produced under generally similar conditions from different multipolymer blend combinations, as follows: Sample A: a 26 g/m$^2$ spunbond fabric consisting of 96% isotactic polypropylene and 4% polyethylene (Dow 05862N); Sample B: a 33 g/m$^2$ spunbond fabric consisting of 76% isotactic polypropylene, 20% propylene copolymer (Montell KSO57P), and 4% polyethylene (Dow 05862N); Sample C: a 33 g/m$^2$ spunbond fabric consisting of 85% polyethylene (Dowlex 2553) and 15% ethylene-propylene copolymer (Amoco 8352); and Sample D: a 60 g/m$^2$ spunbond-meltblown-spunbond composite fabric consisting of bicomponent spunbond filaments (polyester core, polyethylene sheath) and meltblown polyethylene. The fabric tensile strength and peak elongation properties were measured in the machine direction (MD) and in the cross-machine direction (CD) according to ASTM D-1682. The Taber abrasion resistance of the fabrics were measured according to ASTM D-3884, using both the rubber wheel test and the felt wheel test. The results are shown in Table 1 below. For comparison, a commercially available 100% isotactic polypropylene spunbond fabric produced by Fiberweb North America under the trademark Celestra®, was also tested, and reported in Table 1 as Sample E. It was not tested for fuzz, since it failed the elongation criteria.

EXAMPLE 2

Ninety percent by weight of a linear low density polyethylene (LLDPE) with a melt flow of 27 (Dow 6811 LLDPE) and ten percent by weight of a polypropylene (PP) polymer with a melt flow approximately 35 (Aristech CP 350 J) were dry blended in a rotary mixer. The dry-blended mixture was then introduced to the feed hopper of a spunbond nonwoven spinning system. Continuous filaments were meltspun by a slot draw process at a filament speed of approximately 600 m/min and deposited upon a collection surface to form a spunbond nonwoven web, and the web was thermally bonded using a patterned roll with 12% bond area. For comparison purposes, nonwoven spunbond fabrics were produced under similar conditions with the same polymers, using 100% PP and 100% LLDPE.

As shown in Table 2, the 100% LLDPE spunbond samples exhibited superior softness (75 and 77.5) compared to the 100% polypropylene spunbond sample (30). However, the abrasion resistance of the 100% LLDPE sample, as seen from the higher fuzz measurement (12.5 and 2.4), was relatively poorer compared to the 100% PP sample (0.3). The nonwoven fabric formed from the 90% LLDPE/10%PP blend had a high softness (67.5) only slightly less than the 100% LLDPE fabric, and had abrasion resistance (fuzz value) of 1.0 mg, which is significantly better than the values seen for 100% LLDPE. The blend sample also showed improved CD tensile compared to products made with 100% LLDPE.

TABLE 2

| Sample | A | B | C | D |
|---|---|---|---|---|
| C = comparison I = invention Composition: | C | C | C | I |
| % polypropylene | 100 | 0 | 0 | 10 |
| % polyethylene | 0 | 100 | 100 | 90 |
| filament dia. (microns) | 17.5 | 20.9 | 20.9 | 22.5 |
| Basis weight (gsm)$^1$ | 23.1 | 25.2 | 24.6 | 24.8 |
| Loft @ 95 g/in$^2$ (mils)$^2$ | 9.8 | 9.0 | 7.8 | 9.3 |
| Fuzz (mg)$^3$ | 0.3 | 12.5 | 2.4 | 1.0 |
| Softness$^4$ | 30 | 75 | 77.5 | 67.5 |

TABLE 1

Physical Properties of High Elongation Multi-Polymer Nonwoven Fabrics

| Sample | MD tensile (g/cm) | CD Tensile (g/cm) | MD Elong. (%) | CD Elong. (%) | Taber Abrasion (cycles) | |
|---|---|---|---|---|---|---|
| | | | | | Rubber Wheel | Felt Wheel |
| A | 1144 | 307 | 132 | 121 | 79 | 800 |
| B | 1325 | 578 | 215 | 191 | 71 | 1050 |
| C | 610 | 263 | 141 | 188 | 124 | 1300 |
| D | 1764 | 507 | 154 | 133 | 127 | 2650 |
| E | 768 | 553 | 38 | 44 | nt* | nt* |

*nt = not tested. This material fails the elongation criteria and therefore was not tested for fuzz.

TABLE 2-continued

| Sample | A | B | C | D |
|---|---|---|---|---|
| Strip Tensile (g/cm)[5] | | | | |
| CD | 557 | 139 | 157 | 164 |
| MD | 1626 | 757 | 639 | 467 |
| Peak Elongation (%) | | | | |
| CD | 90 | 116 | 129 | 108 |
| MD | 93 | 142 | 106 | 119 |
| TEA (in.g./in | | | | |
| CD | 852 | 297 | 346 | 354 |
| MD | 2772 | 2222 | 1555 | 1389 |

[1] gsm = grams per square meter
[2] Loft was determined by measuring the distance between the top and the bottom surface of the fabric sheet while the sheet was under compression loading of 95 grams per square inch. The measurement is generally the average of 10 measurements.
[3] Fuzz is determined by repeatedly rubbing a soft elastomeric surface across the face of the fabric a constant number of times. The fiber abraded from the fabric surface is then weighed. Fuzz is reported as mg weight observed.
[4] Softness was evaluated by an organoleptic method wherein an expert panel compared the surface feel of Example Fabrics with that of controls. Results are reported as a softness score with higher values denoting a more pleasing hand. Each reported value is for a single fabric test sample, but reflects the input of several panel members.
[5] Tensile, Peak Elongation and TEA were evaluated by breaking a one inch by seven inch long sample generally following ASTM D1682-64, the one-inch cut strip test. The instrument cross-head speed was set at 5 inches per minute and the gauge length was set at 5 inches per minute. The Strip Tensile Strength, reported as grams per centimeter, is generally the average of at least 8 measurements. Peak Elongation is the percent increase in length noted at maximum tensile strength. TEA, Total Tensile Energy Absorption, is calculated from the area under the stress-strain curve generated during the Strip Tensile test.

EXAMPLE 3
(Control)

A control fiber was made by introducing 100% Dow LLDPE 2500 (55 MI, 0.923 density) to a feed hopper of a spinning system equipped with an extruder, a gear pump to control polymer flow at 0.75 gram per minute per hole, and a spinneret with 34 holes of L/D=4:1 and a diameter of 0.2 mm. Spinning was carried out using a melt temperature in the extruder of 215° C. and a pack melt temperature of 232° C. After air quench, the resulting filaments were drawn down at a filament speed of approximately 1985 m/min using an air aspiration gun operating at 100 psig to yield a denier of 3.01 and denier standard deviation of 0.41.

EXAMPLE 4

Ninety parts by weight of Dow LLDPE Type 2500 (55 MI, 0.923 density) and ten parts of Himont X10054-12-1 polypropylene (65 MFR) were dry blended in a rotary mixer and then introduced to the feed hopper of the spinning system described in Example 3. Spinning was carried out using a pack melt temperature of 211° C. After air quench, the resulting filaments were drawn down at a filament speed of approximately 2280 M/Min using an air aspiration gun operating at 100 psig to yield a denier of 2.96 and a denier standard deviation of 1.37.

EXAMPLE 5

Ninety parts by weight of Dow LLDPE Type 2500 (55 MI, 0.923 density) and ten parts of Soltex 3907 polypropylene (35 MFR, 1.74 die swell, CR grade) were dry blended in a rotary mixer and then introduced to the feed hopper of the spinning system described in Example 3. Spinning was carried out using a pack melt temperature of 231° C. and an extruder melt temperature of 216° C. After air quench, the resulting filaments were drawn down at a filament speed of approximately 2557 M/Min using an air aspiration gun operating at 100 psig to yield a denier of 2.64 and a denier standard deviation of 0.38.

EXAMPLE 6

Ninety parts by weight of Dow LLDPE Type 6808A (36 MI, 0.940 density) and ten parts of Soltex 3907 polypropylene (35 MFR, 1.74 die swell, CR grade) were dry blended in a rotary mixer and then introduced to the feed hopper of the spinning system described in Example 3. Spinning was carried out using a pack melt temperature of 231° C. and an extruder melt temperature of 216° C. After air quench, the resulting filaments were drawn down at a filament speed of approximately 2129 M/Min using an air aspiration gun operating at 100 psig to yield a denier of 3.17 and a denier standard deviation of 2.22.

The quality of spinning for a given formulation has been found to roughly correlate with the denier standard deviation. A reduced standard deviation suggests more stable or higher quality spinning. Thus it is unexpected and contrary to the teaching of the prior art that the blend using a 35 MFR polypropylene in Example 5 yielded a more stable spinning than seen with the corresponding LLDPE control in Example 3.

EXAMPLE 7

Eighty parts by weight of a linear low density polyethylene pellets of 55 melt index and 0.925 g/cc density and twenty parts by weight polypropylene pellets of 35 melt flow rate were dry blended in a rotary mixer. The dry-blended mixture was then introduced to the feed hopper of a spinning system equipped with an extruder with a 30:1 l/d ratio, a static mixer, and a gear pump for feeding the molten polymer to a heated melt block fitted with a spinneret. Filaments were extruded from the spinneret and drawn using air aspiration.

EXAMPLE 8

Samples of continuous filament spunbonded nonwoven webs were produced from blends of a linear low density polyethylene with a melt index of 27 (Dow 6811A LLDPE) and a polypropylene homopolymer (Appryl 3250YR1, 27 MFR) in various blend proportions. Control fabrics of 100 percent polypropylene and 100 percent polyethylene were also produced under similar conditions. The fabrics were produced by melt spinning continuous filaments of the various polymers or polymer blends, attenuating the filaments pneumatically by a slot draw process, depositing the filaments on a collection surface to form webs, and thermally bonding the webs using a patterned calender roll with a 12 percent bond area. The fabrics had a basis weight of approximately 25 gsm and the filaments had an average mass/length of 3 dtex. The tensile strength and elongation properties of these fabrics and their abrasion resistance were measured, and these properties are listed in Table 3. As shown, the 100 percent polypropylene control fabric had excellent abrasion resistance, as indicated by no measurable fuzz generation; however the fabrics have relatively low elongation. The 100 percent polyethylene control fabric exhibited good elongation properties, but very poor abrasion resistance (high fuzz values and low Taber abrasion resistance) and relatively low tensile strength. Surprisingly, the fabrics made of blends of polypropylene and polyethylene exhibited an excellent combination of abrasion resistance, high elongation, and good tensile strength. It is noted that the CD elongation values of the blends actually exceed that of the 100% polyethylene control. This surprising increase in elongation is believed to be attributable to the better bonding of the filaments of the blend as compared to the bonding achieved in the 100% polyethylene control, which resulted in the fabrics making good use of the highly elongatable filaments without bond failure.

EXAMPLE 9

Samples of continuous filament spunbonded nonwoven webs of basis weight approximately 25 grams/square meter were produced from blends of a linear low density polyethylene with a melt index of 27 (Dow 6811A LLDPE) and a polypropylene homopolymer (either Appryl 3250 YR1 or Aristech CP350J) in various blend proportions. Control fabrics of 100 percent polypropylene and 100 percent polyethylene were also produced under similar conditions. The fabrics were produced by melt spinning continuous filaments of the various polymers or polymer blends, attenuating the filaments pneumatically by a slot draw process, depositing the filaments on a collection surface to form webs, and thermally bonding the webs using a patterned calender roll with a 12 percent bond area. The tensile strength and elongation properties of these fabrics and their abrasion resistance were measured, and these properties are listed in Table 3. As shown, the 100 percent polypropylene control fabric had excellent abrasion resistance, as indicated by no measurable fuzz generation; however the fabrics had very low elongation, thus limiting the utility of such fabrics in extensible film/fabric laminates. The 100 percent polyethylene control fabric exhibited excellent elongation properties, but very poor abrasion resistance (high fuzz values) and relatively low tensile strength. Surprisingly, the fabrics made of polypropylene/polyethylene blends exhibited an excellent combination of abrasion resistance, high elongation, and good tensile strength. The high filament elongation makes the fabrics well suited for use in an extensible film/fabric composite structure.

EXAMPLE 10

A polyethylene film of approximately 1.5 mil thickness, such as is used in a disposable diaper backsheet, was sprayed with an all purpose adhesive (Locktite Corporation) and was bonded by application of pressure to a 25 gsm spunbond fabric containing 15% polypropylene and 85% polyethylene, one of the nonwoven fabrics described in Example 9. The cross machine direction of the fabric coincided with the cross machine direction of the film. The composite fabric of film and polypropylene/polyethylene spunbond nonwoven was then extended to 200% extension in the CD direction, beyond the elastic limit of the spunbond fabric, by an Instron tensile tester. The resulting elongated composite fabric was found to exhibit reduced basis weight, desirable softness and drape properties, and was surprisingly free of detached fibers and lint, thus showing no unsightly fuzzed appearance. The extended composite fabric was thicker in appearance than its unextended precursor. The elongated fabric can be used as a diaper backside or diaper leg cuffs.

TABLE 3

MECHANICAL PROPERTIES OF POLYPROPYLENE (PP)/POLYETHYLENE (PE) BLEND FABRICS

| Fabric | MD Tensile (g/cm)[6] | CD Tensile (g/cm)[6] | MD Elong (%)[6] | CD Elong (%)[6] | Fuzz (mg)[7] | Taber Abrasion (cycles-rubber wheel)[8] | Taber Abrasion (cycles-felt wheel)[8] |
|---|---|---|---|---|---|---|---|
| 100% PP | 925 | 405 | 62 | 70 | 0.0 | 40 | 733 |
| 50/50 PP/PE | 1110 | 415 | 147 | 145 | 0.3 | — | — |
| 25/75 PP/PE | 764 | 273 | 170 | 190 | 0.3 | 32 | 200 |
| 15/85 PP/PE | 676 | 277 | 199 | 224 | 0.5 | 22 | 500 |
| 10/90 PP/PE | 426 | 170 | 109 | 141 | 0.3 | — | — |
| 100% PE | 296 | 63 | 168 | 131 | 19.0 | 10 | 15 |

[6]Tensile and Peak Elongation were evaluated by breaking a one inch by seven inch long sample generally following ASTM D1682-64, the one-inch cut strip test. The instrument cross-head speed was set at 5 inches per minute and the gauge length was set at 5 inches per minute. The Strip Tensile Strength, reported as grams per inch, is generally the average of at least 8 measurements. Peak Elongation is the percent increase in length noted at maximum tensile strength.
[7]Fuzz is determined by repeatedly rubbing a soft elastomeric surface across the face of the fabric a constant number of times. The fiber abraded from the surface is then weighed. Fuzz is reported as mg weight observed.
[8]Conducted according to ASTM D3884-80 where the number of cycles was counted until failure. Failure was defined as the appearance of a hole of one square millimeter or greater in the surface of the fabric.

EXAMPLE 11

Figure 6B:
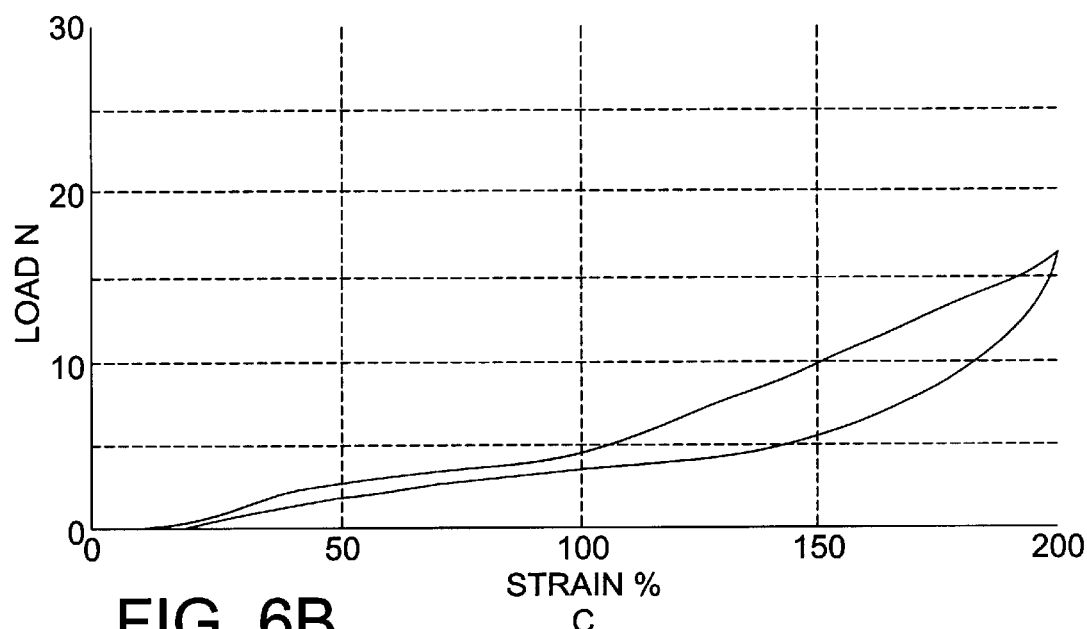

An elastic film of 1.5 mil thickness was cast from Hytrel 8122 polyester elastomer sold by E. I. Du Pont DeNemours Company. A sample of the elastic film was sprayed with an all purpose adhesive (Locktite Corporation) and was bonded by application of pressure to a 25 grams per square meter spunbonded fabric containing 15% polypropylene and 85% polyethylene (one of the nonwoven fabric samples described in Example 9). The cross machine direction of the fabric coincided with the machine direction of the film. A 1.5 inch wide sample of the resulting composite was placed in the jaws of an Instron tensile tester and elongated to 200% extension. The composite was returned to 0% extension. The resulting stress strain curve is given in FIG. 6A. The spunbonded component remained attached to the elastic film but the filaments were elongated, so that the unextended composite had a bulky appearance. The composite was elongated a second time to 200% extension and then returned to 0% extension. The resulting stress strain curve is given in FIG. 6B. The modulus of elasticity was much lower for the second extension, because the filaments of the spunbonded component were no longer resisting the extension. The composite had stretch behavior characteristic of an elastic material.

EXAMPLE 12

A fabric (Fabric A) was prepared by thermal point bonding three polyolefin webs placed in juxtaposition. These webs were melt spun from the following polymers:

Outer layer #1  8.5 grams per square meter 96% polypropylene (Exxon 3445)/4% polyethylene (Dow 05862N)
Middle Layer  2 grams per square meter 100% polypropylene (Exxon 3546G) meltblown fibers -continued Outer layer #2  8.5 grams per square meter 96% polypropylene (Exxon 3445)/4% polyethylene (Dow 05862N)

The average fiber size in the outer layers was 3.3 dtex. The average fiber diameter in the middle layer was 1.9 microns. The webs were bonded using a set of calender rolls with 17% bond area. The mechanical properties of this fabric, as well as those of a control fabric made of 100% polypropylene (Fabric B) are given in Table 3. were evaluated. The higher elongation of the fabric containing polyethylene in the filaments of the outer layers is clearly evident.

A sample of this trilaminate fabric (Fabric A) is inserted as a barrier cuff component into a diaper of the design described in U.S. Pat. No. 4,738,677. This diaper also incorporates a fastening system as described in U.S. Pat. No. 5,242,436. In this diaper, the above polyolefin trilaminate (Fabric A) is adhesively attached to a section of elastic foam in the side panel region of the diaper. The resulting elastic laminate is subjected to 33% extension. The thermal point thermal bonds of the inelastic trilaminate component remain intact while the filaments connecting the bonds are elongated. The result is that the side panel section of the diaper becomes stretchable, the elastic foam dominating its stress-strain characteristics.

EXAMPLE 13

Spunbond-meltblown-spunbond trilaminate fabrics were produced using spunbond outer webs of continuous filament multipolymer fibers of 4% polyethylene and 96% polypropylene and an inner extensible web of polypropylene meltblown microfibers having a maximum fiber diameter of 5 microns. The composite fabric was bonded by passing it through a heated calender at a temperature of 145° C. with the patterned roll of the calender producing a bond area of about 17 percent. The trilaminate fabrics were tested for tensile properties and the barrier properties of the composites were measured by a rising water column strikethrough test. The results are shown in Table 4.

the minor phase and the fiber core consists of a single polypropylene or copolypropylene polymer. The abrasion resistance properties of such fibers can then be compared to nonwovens made with fibers not of this invention, such fabrics made with mono and bicomponent fibers where each mono or bicomponent aspects of the fiber is made using a single polymer.

Continuous filament spunbond nonwoven fabrics of this invention and comparative fabrics were produced on a pilot line equipped with two extruders; spin pack and spinnerets able to spin bicomponent fibers; a quench zone to promote the transition of the fiber from the liquid to the solid state; an attenuation zone where the fibers are accelerated to promote drawing to build mechanical stretch and achieve low denier below 5 denier for softness and desired hand; a moving wire to collect the fibers after draw down; and a thermal bonding calendar where the web of collected fibers is bonded together by heat and compression between a smooth roll and an embossed roll. Reference is made to U.S. Pat. No. 5,162,074, which teaches one method for constructing spin packs to spin bicomponent fibers. The embossing calendar in this pilot line has a bond area of approximately 18% with approximately 144 emboss points per square inch.

For these experiments the attenuation zone of the pilot line was equipped with a Lurgi DOCON draw system. In the Lurgi method the filaments are extruded from the spinnerets, quenched via cool moving air and then introduced into tubes where the fibers are accelerated via contact with high pressure air to allow fiber draw down to denier per filament below 5. At the bottom of the tubes the filaments are separated from each other and sprayed onto the moving wire.

The abrasion resistance of the resulting thermal bonded fabrics was measured by subjecting the fabric to a modified Sutherland Ink Rub Test. The Sutherland Ink Rub Test is described in ASTM D-5264, "Standard Practice for Abrasion Resistance for Printed Materials by the Sutherland Ink Rub Tester." For evaluation of fabric abrasion resistance the fabric to be tested is mounted in the Sutherland tester such that the rub tester moved across the fabric in the cross machine (CD) direction. For these tests the 2-pound tester

TABLE 4

| Sample | | F | G | H | I |
| --- | --- | --- | --- | --- | --- |
| Total basis weight (g/m²) | | 19.21 | 20.2 | 23.45 | 22.1 |
| Thickness (mm) | | 0.181 | | 0.22 | |
| Spunbond denier (dpf) | top | 3.5 | 3.0 | 3.0 | 3.3 |
| | Bottom | 3.0 | | 3.5 | |
| Meltblown fiber dia. (microns) | top | 1.95 | | 1.69 | |
| | Bottom | 1.74 | | 1.75 | |
| Tensile strength (g/in) | MD | 1828 | 1439.0 | 1836.0 | 1504.0 |
| | CD | 424.4 | 512.4 | 530.7 | 588.8 |
| Max. elongation (%) | MD | 97.9 | 113.6 | 100.5 | 97.8 |
| | CD | 82.0 | 95.9 | 81.1 | 82.2 |
| Break elongation (%) | MD | 113.5 | 127.9 | 116.3 | 108.3 |
| | CD | 116.5 | 135.8 | 105.5 | 114.2 |
| TEA (cm-g/cm²) | MD | 627.6 | 526.0 | 648.4 | 485.4 |
| | CD | 123.2 | 201.2 | 151.1 | 203.2 |
| Rising water column (MM) | | 111.9 | 11.6 | 209.9 | 246 |

EXAMPLE 14

This example illustrates the preparation and the benefits of fabrics made with continuous bicomponent fibers of this invention, where the sheath is formed from a blend of a specific grade of polyethylene as the dominant phase mixed with a specific grade of polypropylene or copolyethylene as foot was used and the machine was set to complete 5 cycles. A fine grit sandpaper was used as the abrasive material. When the test was complete all broken fibers were carefully collected and weighed using an analytical balance to provide a quantitative estimate of extent of damage to the fabric. It is assumed that the lower weight of recovered broken fibers the more resistant the nonwoven is to abrasion damage.

Examples 1–5 are comparative examples and Examples 6–9 illustrate various advantageous embodiments of the invention.

Example 1 was made using the above pilot line by spinning a single polymer, the commercially available polypropylene AMOCO Type 7956, with melt flow of 35. The Sutherland Ink Rub test gave an abrasion resistance value of 0.102.

Example 2 was made using the above pilot line such that polyethylene, type DOW 6811A with melt index of 27 was extruded in one extruder to become the sheath and polypropylene, type AMOCO 7957 with melt flow of 35, was extruded in the second extruder to make the core thus yielding a ratio of 20/80 sheath/core in the bicomponent fibers for the nonwoven Example 2. The Sutherland Ink Rub test gave an abrasion resistance value of 0.205.

Example 3 was made using the above pilot line such that polyethylene, type DOW 6811A, was extruded in one extruder to become the sheath and polypropylene, type AMOCO 7957, was extruded in the second extruder to make the core thus yielding a ratio of 80/20 sheath/core in the bicomponent fibers for the nonwoven Example 3. The Sutherland Ink Rub test gave an abrasion resistance value of 0.220.

Example 4 was made using the above pilot line such that polyethylene, type DOW 6811A, was extruded in one extruder to become the sheath and polypropylene, type AMOCO 7644, was extruded in the second extruder to make the core thus yielding a ratio of 50/50 sheath/core in the bicomponent fibers for the nonwoven Example 4. The Sutherland Ink Rub test gave an abrasion resistance value of 0.149.

Example 5 was BBA COROLINE Spunbond Polyethylene fabric (100% polyethylene) with basis weight of 40 gsm commercially available from BBA Nonwovens, Berlin, Germany. The Sutherland Ink Rub test gave a value of 0.168.

Example 6 was made using the above pilot line such that a blend of 85% polyethylene, type DOW 2553 with a melt index of 40 and 15% of the polypropylene APPRYL 3250 with a melt flow of 26, was extruded in one extruder to become the sheath and polypropylene, type APPRYL 3250, was extruded in the second extruder to make the core thus yielding the ratio of 50/50 sheath/core in the bicomponent fibers for the nonwoven Example 6. The blend used for the sheath was mixed as dry pellets in a cement mixer before being introduced into the hopper to feed the extruder. The Sutherland Ink Rub test gave an abrasion resistance value of 0.155.

Example 7 was made using the above pilot line such that a blend of 85% polyethylene, type DOW 6811A with melt index of 27 and 15% of the polypropylene APPRYL 3250 with a melt flow of 26, was extruded in one extruder to become the sheath and polypropylene, type APPRYL 3250, was extruded in the second extruder to make the core thus yielding the ratio of 50/50 sheath/core in the bicomponent fibers for the nonwoven Example 7. The blend used for the sheath was mixed as dry pellets in a cement mixer before being introduced into the hopper to feed the extruder. The Sutherland Ink Rub test gave an abrasion resistance value of 0.143.

Example 8 was made using the above pilot line such that a blend of 85% polyethylene, type DOW 6811A with melt index of 27 and 15% of the polypropylene APPRYL 3250 with a melt flow of 26, was extruded in one extruder to become the sheath and polypropylene, type AMOCO 7956, was extruded in the second extruder to make the core thus yielding the ratio of 50/50 sheath/core in the bicomponent fibers for the nonwoven Example 8. The blend used for the sheath was prepared by mixing the components together, melting in an extruder to yield a molten mixture then extruding as pellets to be introduced into the pilot line hopper to feed the pilot line extruder. The Sutherland Ink Rub test gave an abrasion resistance value of 0.132.

Example 9 was made using the above pilot line such that a blend of 85% polyethylene, type DOW 6811A with melt index of 27 and 15% of the copolypropylene type AMOCO 8253, a random copolymer of propylene in the ratio of 97/3 with melt flow of 6, was extruded in one extruder to become the sheath and polypropylene, type AMOCO 7956 with melt flow of 35, was extruded in the second extruder to make the 1 5 core thus yielding the ratio of 50/50 sheath/core in bicomponent fibers for the nonwoven Example 9. The blend used for the sheath was mixed as dry pellets in a cement mixer before being introduced into the hopper to feed the extruder. The Sutherland Ink Rub test gave an abrasion resistance value of 0.106.

EXAMPLE 15

This example illustrates the preparation and the benefits of fabrics made with continuous bicomponent fibers of this invention, wherein the core is formed from a multipolymer blend of at least two different polyolefin polymers, the polymers being present as a higher-melting dominant continuous phase and at least one lower-melting noncontinuous phase dispersed therein. The higher-melting continuous phase includes a propylene polymer and the lower-melting noncontinuous phase includes a polyethylene polymer.

Continuous filament spunbond nonwoven fabrics of this invention and comparative fabrics were produced on a pilot line equipped with two extruders; spin pack and spinnerets able to spin bicomponent fibers; a quench zone to promote the transition of the fiber from the liquid to the solid state; an attenuation zone where the fibers are accelerated to promote drawing to build mechanical strength and achieve low denier below 5 denier for softness and desired hand; a moving wire to collect the fibers after draw down; and a thermal bonding calendar where the web of collected fibers is bonded together by heat and compression between a smooth roll and an embossed roll. Reference is made to U.S. Pat. No. 5,162,074, which teaches one method for constructing spin packs to spin bicomponent fibers. The embossing calendar in this pilot line has a bond area of approximately 18% with approximately 144 emboss points per square inch.

For these experiments the attenuation zone of the pilot line was equipped with a Lurgi DOCON draw system. In the Lurgi method the filaments are extruded from the spinnerets, quenched via cool moving air and then introduced into tubes where the fibers are accelerated via contact with high pressure air to allow fiber draw down to denier per filament below 5. At the bottom of the tubes the filaments are separated from each other and sprayed onto the moving wire.

The abrasion resistance of the resulting thermal bonded fabrics was measured by subjecting the fabric to a modified Sutherland Ink Rub Test. The Sutherland Ink Rub Test is described in ASTMD-5264, "Standard Practice for Abrasion Resistance of Printed Materials by the Sutherland Ink Rub Tester." For evaluation of fabric abrasion resistance the fabric to be tested is mounted in the Sutherland tester such that the rub tester moved across the fabric in the CD direction. For these tests the 2-pound tester foot was used and the machine was set to complete 5 cycles. A fine grit sandpaper was used as the abrasive material. When the test was complete all broken fibers were carefully collected and weighed using an analytical balance to provide a quantitative estimate of extent of damage to the fabric. It is assumed that the lower the weight of recovered broken fibers the more resistant the nonwoven is to abrasion damage. Examples 1, 2 and 7 are comparative examples and Examples 3–6 illustrate various advantageous embodiments of the invention.

Example 1 was made using the above pilot line by spinning a single polymer, the commercially available polypropylene AMOCO Type 7956, with melt flow of 35. The Sutherland Ink Rub test gave an abrasion resistance value of 0.102.

Example 2 was made using the above pilot line such that polyethylene, type DOW 6811A, with melt index of 27 was extruded in one extruder to become the sheath and polypropylene, type AMOCO 7956, with melt flow of 35, was extruded in the second extruder to make the core thus yielding a ratio of 80/20 sheath/core in the bicomponent fibers for the nonwoven Example 2. The basis weight of Example 2 was found to be 33 grams per square meter. The Sutherland Ink Rub test for Example 2 gave an abrasion resistance value of 0.146 when rubbed as described above in the CD direction. The Sutherland Ink Rub test was then repeated as described above but now the rubbing was in the MD of the fabric to yield an abrasion resistance value of 0.115. Mechanical properties of Example 2 were also measured generally following ASTMD 1682, "Breaking load and Elongation of Textile Fabrics" using the one inch Strip Test method. CD tensile equaled 763 grams. CD Elongation at maximum tensile was 134%. CD Toughness at maximum tensile was 742 inch-grams/inch squared. MD tensile equaled 2213 grams. MD Elongation at maximum tensile was 121%. MD Toughness at maximum tensile was 2320 inch-grams/inch squared.

Example 3 was made using the above pilot line such that polyethylene, type DOW 6811A, with melt index of 27 was extruded in one extruder to become the sheath and a blend of 76% polypropylene, type AMOCO 7956, plus 20% MONTELL KSO84P Catalloy® plus 4% polyethylene, DOW 5862, was extruded in the second extruder to make the core thus yielding a ratio of 80/20 sheath/core in the bicomponent fibers for the nonwoven Example 3. The basis weight of Example 3, was found to be 29 grams per square meter. The Sutherland Ink Rub test for Example 3 gave an abrasion resistance value of 0.104 when rubbed as described above in the CD direction. The Sutherland Ink Rub test was then repeated as described above but now the rubbing was in the MD of the fabric to yield an abrasion resistance value of 0.149.

Mechanical properties of Examples 3 were also measured generally following ASTMD 1682, "Breaking load and Elongation of Textile Fabrics" using the one inch Strip Test method. CD tensile equalied 858 grams. CD Elongation at maximum tensile was 134%. CD Toughness at maximum tensile was 842 inch-grams/inch squared. MD tensile equaled 2184 grams. MD Elongation at maximum tensile was 106%. MD Toughness at maximum tensile was 2067 inch-grams/inch squared.

Example 4 was made using the above pilot line such that polyethylene, type DOW 6811A, with melt index of 27 was extruded in one extruder to become the sheath and a blend of a random copolymer made from propylene 97% and ethylene 3% available as Type AMOCO 8956 plus 20% MONTELL KSO84P Catalloy® plus 4% polyethylene, DOW 5862, was extruded in the second extruder to make the core thus yielding a ratio of 80/20 sheath/core in the bicomponent fibers for the nonwoven Example 4. The basis weight of Example 4 was found to be 29 grams per square meter. The Sutherland Ink Rub test for Example 4 gave an abrasion resistance value of 0.1146 when rubbed as described above in the CD direction. The Sutherland Ink Rub test was then repeated as described above but now the rubbing was in the MD of the fabric to yield an abrasion resistance value of 0.132. Mechanical properties of Example 4 were also measured generally following ASTMD 1682, "Breaking load and Elongation of Textile Fabrics" using the one inch Strip Test method. CD tensile equaled 770 grams. CD Elongation at maximum tensile was 157%. CD Toughness at maximum tensile was 873 inch-grams/inch squared. MD tensile equaled 1749 grams. MD Elongation at maximum tensile was 133%. MD Toughness at maximum tensile was 1981 inch-grams/inch squared.

Example 5 was made using a commercial Lurgi Spunbond Line similar to the above described pilot line but larger in scale and having two beams of spinnerets. Both beams of spinnerets produced the same fibers as described below. Example 5 was made such that polyethylene, type DOW 6811A, with melt index of 27 was extruded in one extruder to become the sheath and a blend of 76% a random copolymer made from propylene 97% and ethylene 3% available as Union Carbide 6D43 plus 20% MONTELL Adflex 357 Catalloy® plus 4% polyethylene, DOW 5862 N, was extruded in the second extruder to make the core thus yielding a ratio of 80/20 sheath/core in the bicomponent fibers for the nonwoven Example 5. The basis weight of Example 5 was found to be 30 grams per square meter. Mechanical properties of Example 5 were also measured generally following ASTMD 1682, "Breaking load and Elongation of Textile Fabrics" using the one inch Strip Test method. CD tensile equaled 1089 grams. CD Elongation at maximum tensile was 82%. CD Toughness at maximum tensile was 680 inch-grams/inch squared. MD tensile equaled 1270 grams. MD Elongation at maximum tensile was 84%. MD Toughness at maximum tensile was 771 inch-grams/inch squared.

Example 6 was made using a very small-scale pilot line similar in function and operation to the above pilot line but much smaller in scale. Example 6 was made such that polyethylene, type DOW 6811A, with melt index of 27 was extruded in one extruder to become the sheath and a blend of 76% polypropylene, type AMOCO 7956 plus 20% MONTELL KSO84P Catalloy® plus 4% polyethylene, DOW 5862, was extruded in the second extruder to make the core thus yielding a ratio of 80/20 sheath/core in the bicomponent fibers for the nonwoven Example 6. The basis weight of Example 6 was found to be 28 grams per square meter. The Sutherland Ink Rub test for Example 6 gave an abrasion resistance values of 0.1366 and 0.1324 when rubbed as described above in the CD direction. Mechanical properties of Example 6 were also measured generally following ASTMD 1682, "Breaking load and Elongation of Textile Fabrics" using the one inch Strip Test method. CD tensile equaled 1113 grams. CD Elongation at maximum tensile was 73%. CD Toughness at maximum tensile was 699 inch-grams/inch squared. MD tensile equaled 859 grams. MD Elongation at maximum tensile was 96%. MD Toughness at maximum tensile was 748 inch-grams/inch squared.

Example 7 was made using a very small-scale pilot line similar in function and operation to the above pilot line but much smaller in scale. Example 7 was made such that polyethylene, type DOW 6811A, with melt index of 27 was extruded in one extruder to become the sheath and polypropylene, type AMOCO 7956 was extruded in the second extruder to make the core thus yielding a ratio of 20/80 sheath/core in the bicomponent fibers for the nonwoven Example 7. The basis weight of Example 7 was found to be 31 grams per square meter. The Sutherland Ink Rub test for Example 7 gave an abrasion resistance values of 0.1366 and 0.1859 when rubbed as described above in the CD direction. Mechanical properties of Example 7 were also measured generally following ASTMD 1682, "Breaking load and Elongation of Textile Fabrics" using the one inch Strip Test method. CD tensile equaled 1418 grams. CD Elongation at maximum tensile was 79%. CD Toughness at maximum tensile was 944 inch-grams/inch squared. MD tensile equaled 931 grams. MD Elongation at maximum tensile was 109%. MD Toughness at maximum tensile was 849 inch-grams/inch squared.

EXAMPLE 16

This example illustrates the preparation and the benefits of fabrics made with continuous bicomponent fibers of this invention, wherein the sheath is formed from a blend of a specific grade of polyethylene as the dominant phase mixed with a specific grade of polypropylene or copolyethylene as the minor phase. Further, the fiber core is formed from a multipolymer blend of at least two different polyolefin polymers, the polymers being present as a higher-melting dominant continuous phase and at least one lower-melting noncontinuous phase dispersed therein. The higher-melting continuous phase includes a propylene polymer and the lower-melting noncontinuous phase includes a polyethylene polymer.

Continuous filament spunbond nonwoven fabrics of this invention are prepared as described in Examples 14 and 15 above, and the abrasion resistance and mechanical properties of the resulting thermal bonded fabrics are measured using the tests described above in Examples 14 and 15.

Fabrics are made using the following polymer blends as the sheath component of bicomponent fibers:

(1) a blend of 85% polyethylene, type DOW 2553 and 15% of the polypropylene APPRYL 3250 with a melt flow of 26;
(2) a blend of 85% polyethylene, type DOW 6811A with melt index of 27 and 15% of the polypropylene APPRYL 3250 with a melt flow of 26; and
(3) a blend of 85% polyethylene, type DOW 6811A with melt index of 27 and 15% of the copolypropylene type AMOCO 8253, a random copolymer of propylene in the ratio of 97/3 with melt flow of 6.

The above fibers included a core component selected from one of the following groups of polymer blends:

(1) a blend of 76% polypropylene, type AMOCO 7956, plus 20% MONTELL KSO84P Catalloy® plus 4% polyethylene, DOW 5862;
(2) a blend of a random copolymer made from propylene 97% and ethylene 3% available as Type AMOCO 8956 plus 20% MONTELL KSO84P Catalloy® plus 4% polyethylene, DOW 5862; and
(3) a blend of 76% a random copolymer made from propylene 97% and ethylene 3% available as Union Carbide 6D43 plus 20% MONTELL Adflex 357 Catalloy® plus 4% polyethylene, DOW 5862 N.

The fibers have sheath/core ratios of 50/50, 80/20, or 20/80. The fabrics exhibit a combination of desirable yet contradictory properties, such as good elongation and aesthetics and desirable tensile strengths. The inventors have found that conventional PE sheath/PP core fibers can have abrasion resistance problems. In contrast fibers such as described in this example can have improved abrasion resistance, as compared to PE/PP sheath core fibers. Although not wishing to be bound by any explanation of the invention, it is believed that the polymer blend sheath component can more strongly bond to other fibers as well as to the core, thus improving fiber tie down and fabric abrasion resistance, yet without sacrificing elongation.

EXAMPLE 17

An investigation was conducted to determine domain size and distribution of the discontinuous polymer phase such as contained within the fiber structure of the fabrics of the invention. Towards that end, a spunbond nonwoven fabric was prepared in accordance with the teachings of the present application. In particular, a polymer blend containing eighty-five percent by weight of a linear low density polyethylene (LLDPE) with a melt index of 27 (Dow 6811A LLDPE) and fifteen percent by weight of a polypropylene (PP) polymer with a melt flow approximately 24 (Appryl 3250 YR1 PP) were dry blended in a rotary mixer. The dry-blended mixture was then introduced to the feed hopper of an extruder of a spunbond nonwoven spinning system. Continuous filaments were meltspun by a slot draw process at a filament speed of approximately 600 m/min and deposited upon a collection surface to form a spunbond nonwoven web, and the web was thermally bonded using a patterned roll with 12% bond area. The sample thus prepared is referred to as Example A.

An alternative method of blending was then employed to produce another fabric sample, referred to as Example B. In Example B the Dow 6811A LLDPE was fed into the main extruder, while the Appryl PP was introduced into the melt stream via a secondary extruder and then passed through a static mixing unit, rather than blending the polymers in the solid state with additional mixing in the extruder, as in Example A. Good mixing was expected to result from both methods. Following extrusion, the procedure used to prepare the spunbonded fabrics of Examples A and B was identical. The fabric in Example B is the same material produced and referenced in Example 8 and Table 3 above.

The spunbond fabric samples were evaluated for polymer domain size and domain distribution based on Transmission Electron Microscopy (TEM) performed on fiber cross sections. In electron microscopy, image contrast is obtained as a result of variation in electron density among the structures present. Most polymers have low atomic number elements such as carbon, hydrogen and oxygen in their main chain and as a result polymers exhibit very little difference in electron density to distinguish between phases in a blend. To overcome this, heavy metal shadowing or staining by addition of a high atomic number element in specific structures is widely used. TEM photomicrographs were prepared for Example A by two independent laboratories. Copies of photomicrographs of the fibers of Example A as evaluated by the two laboratories are attached as FIGS. 7 and 8. TEM photomicrographs were prepared for Example B, and copies of the photomicrographs for Example B are attached as FIG. 9.

Figure 7:
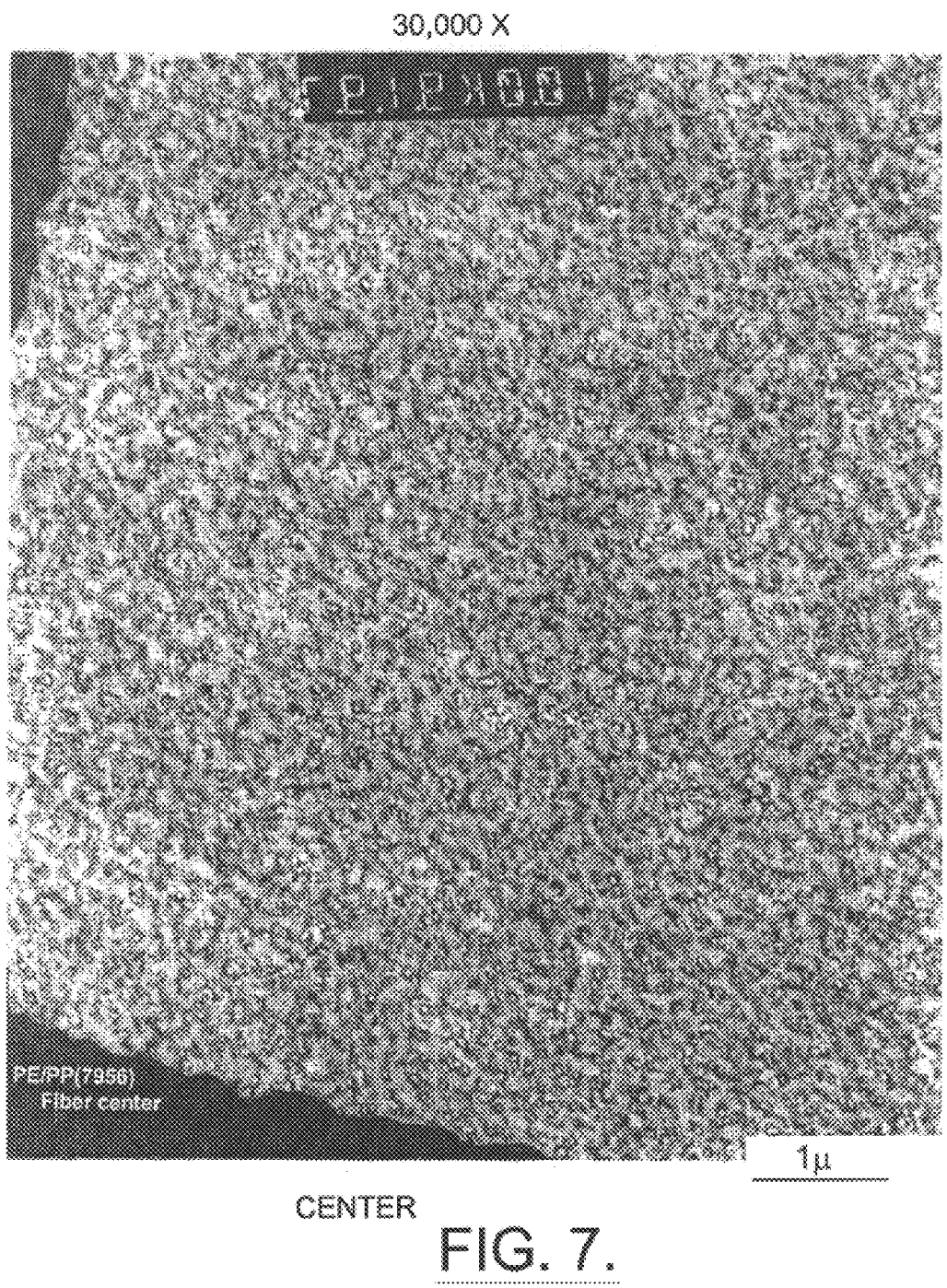
FIGS. 7, 8 and 9 are Transmission Electron Microscopy (TEM) photomicrographs of fibers including a multipolymer blend.
Figure 8:
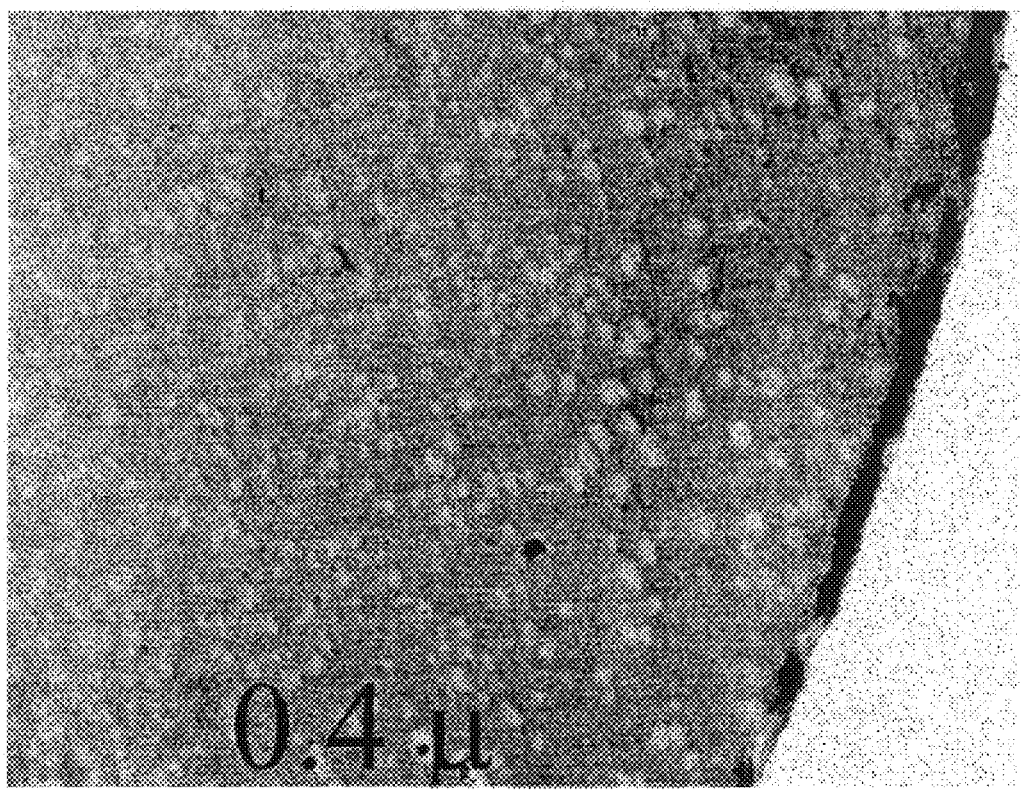
Figure 9:
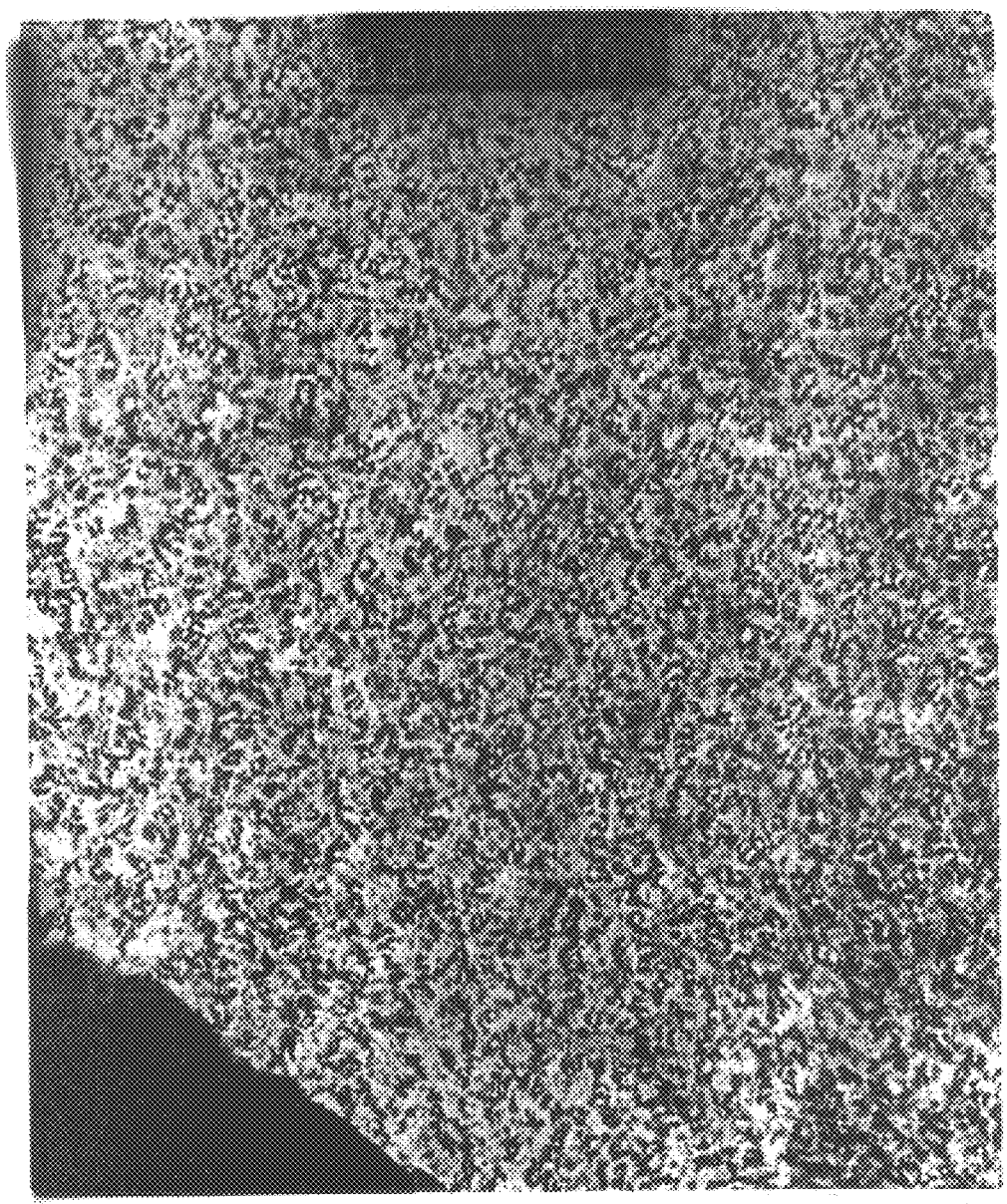

To prepare a spunbond fabric sample for TEM, a small quantity of fabric was embedded in a sample holder and then frozen. A low temperature microtome was used to expose the samples' fiber cross sections without damaging their structure. Ruthenium tetroxide, a heavy metal stain, was then applied to the fractured sample to provide sufficient contrast between the polymer phases. The photomicrographs of FIGS. 7, 8 and 9 are at varying degrees of magnification, as noted thereon (30,000×, 45,000×, and 25,500×, respectively). The domain size range of samples A and B were determined by measuring 50 domains randomly chosen from fiber micrographs illustrating a given fabric sample enlarged 25,000 to 45,000 times.

Figure 10:
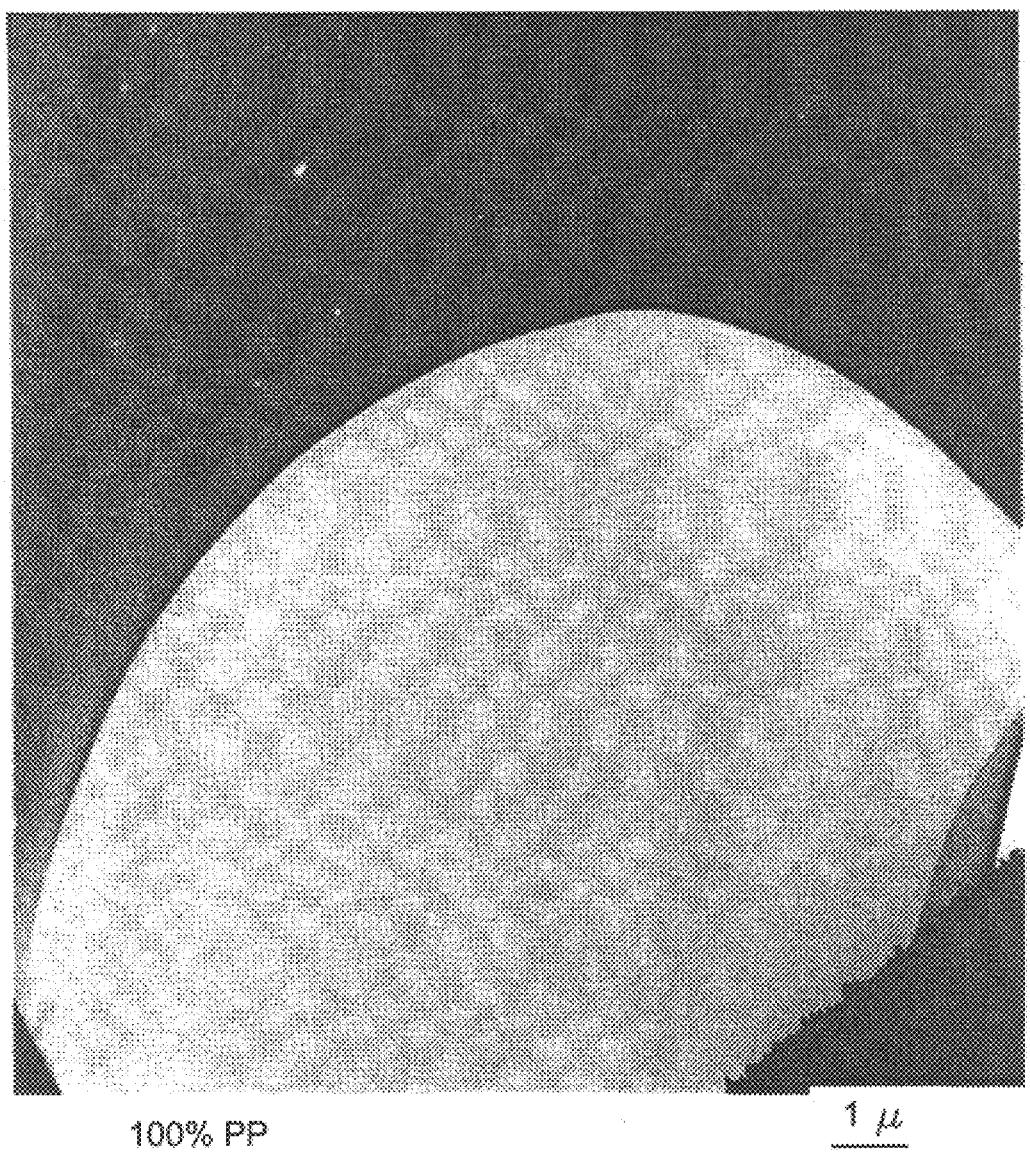
FIGS. 10 and 11 are TEM photomicrographs of fibers formed of 100% polypropylene homopolymer and 100% polyethylene homopolymer, respectively.
Figure 11:
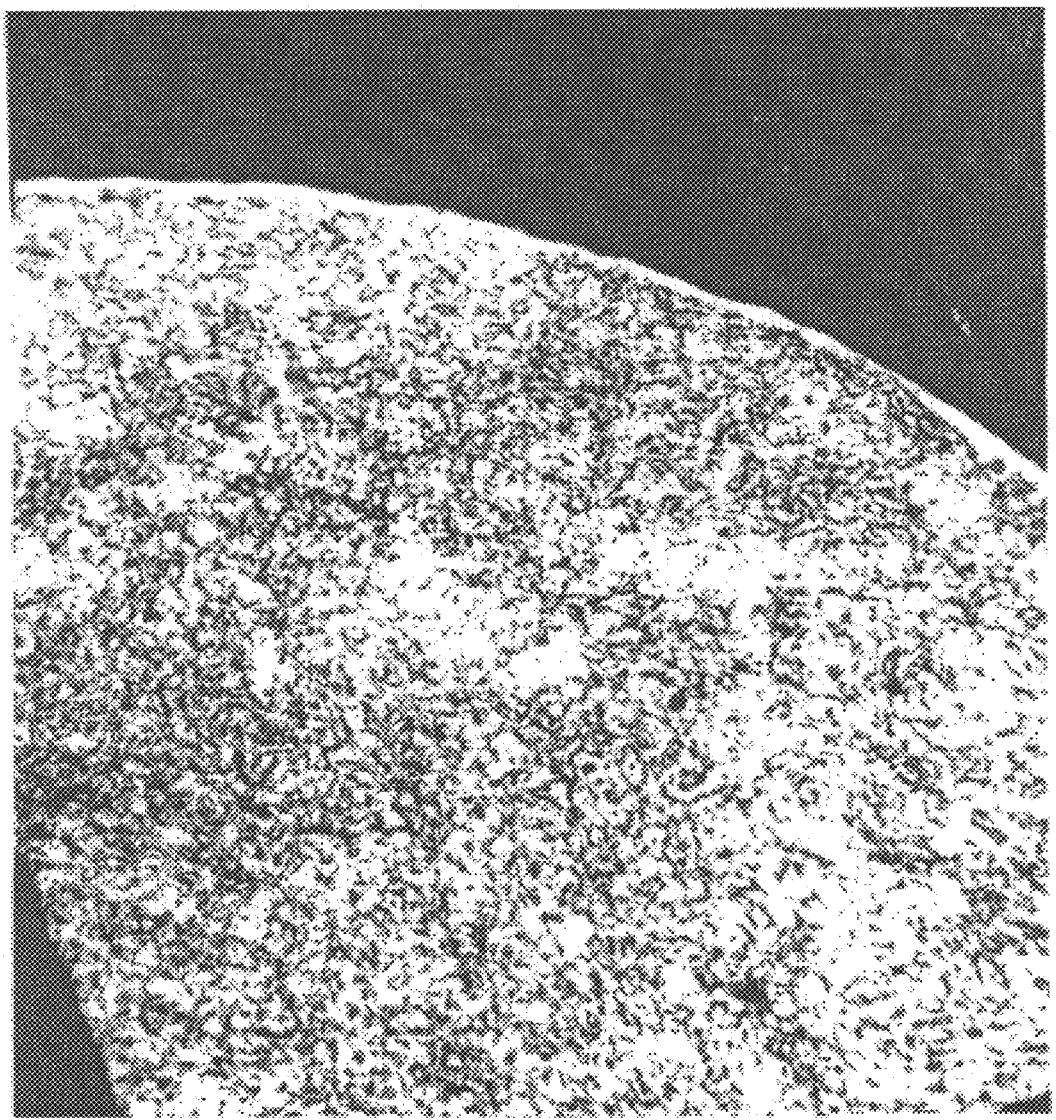

The ruthenium tetraoxide is absorbed into the amorphous regions of the polymer. FIGS. 10 and 11 are TEM photomicrographs of a stained fiber sample from 100% PP homopolymer and 100% PE homopolymer, respectively. FIG. 10 of PP homopolymer shows that the crystallites are so small that the amorphous regions are beyond the resolution of the equipment, thus no contrast is present, and a uniform sample is observed (i.e., no domains or crystallite structure). The TEM photomicrograph of a 100% PE fiber in FIG. 11 illustrates the lamellae structure of PE. The PE crystallites are large enough so that the lamellae texture can be observed if the staining conditions are right. A similar structure resulting from the lamellae structure of PE is superimposed with the domain structure of the blends in FIGS. 7, 8 and 9.

A visual comparison of the photomicrographs clearly shows substantial differences in domain size and distribution of the fibers formed of the blends described in the present application as compared to that reported for other fibers, such as those reported in EP 621,356 (EP '356). The quantitative results from the photomicrographs are provided in the table below. Examples A1, A2 and B all refer to the fibers of the fabrics formed of blends as described in the present application, while C1 refers to information provided EP '356.

| Ex | Material | Domain Size Range (Microns) | Average Domain (Microns) | Domain Distribution |
|----|----------|----------------------------|--------------------------|---------------------|
| A1 | LLDPE/PP | 0.03–0.08 | 0.05 | Uniform |
| A2 | LLDPE/PP | 0.01–0.08 | 0.04 | Uniform |
| B  | LLDPE/PP | 0.02–0.08 | 0.04 | Uniform |
| C  | LLDPE/PP | 0.05–0.30* | — | Stratified |
|    |          | 0.08–0.12** | — | |

*Range of greater than 70% domains
**Range of majority of domains

Based on the foregoing observations, the fibers of the fabrics formed of blends as described in the present application are readily distinguishable from the fibers of EP '356. In particular, the dispersed polymer domains of the fibers of blends as described herein are much smaller than the dispersed polymer domains of the fibers of EP '356. The dispersed polymer domains of the fibers of the fabrics of the blends described in the present application were very small, ranging in size from 0.03 to 0.08 $\mu$m, with an average of 0.05 $\mu$m, for Example A1, 0.01 to 0.08 $\mu$m for Example A2, and 0.02 to 0.08 $\mu$m with an average of 0.04 $\mu$m for Example B. The results for all three exhibits were very similar. The domain size range given is based on the smallest and largest domains observed. The largest domain size observed is simple to measure and quantify, whereas to state the smallest domain size present is much more difficult. Listed in the table are the smallest domain sizes observed in the electron photomicrographs. The electron photomicrographs show extremely small domains and that we are pushing the limits of what can be measured. One skilled in the art would acknowledge that there are most certainly domains that are too small to be observed because they are beyond the resolution of the equipment. The smallest domains are expected to be smaller than that listed in the table.

In contrast, the dispersed polymer domain sizes of the fibers of EP '356 are larger, at least 70% of which are stated to range in size from 0.05 to 0.30 $\mu$m. The domain size range described in the application is very narrow and the average domain size is less than the size range given in EP '356. In addition, the fibers of blends such as described in the present application and the EP '356 fibers differ significantly in domain distribution. The dispersed polymer domains of the fibers of blends as described in the present application were all evenly distributed throughout the cross section of the fiber, meaning that, on average, there is equal distance between a given domain and its nearest neighbor domains. In contrast, FIGS. 1, 9 and 12 of EP '356 illustrate the non-uniform distribution of dispersed polymer domains, and, in particular, the production of stratified domains (FIGS. 9 and 12) and domains concentrated at the periphery of the fiber (FIG. 1).

The presence of smaller polymer domains can be advantageous for fiber extrusion. Likewise, the presence of uniformly distributed domains may be advantageous to fiber production, as the properties of the discontinuous phase are more uniformly distributed throughout the fiber structure. Therefore, one can conclude that the fibers of the present invention differ significantly from the fibers of EP '356.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A multicomponent fiber comprising at least two polymer components arranged in structured domains, at least one of said polymer components comprising a multipolymer blend of at least two different polyolefin polymers, said polymers being present as a lower-melting dominant continuous phase and at least one higher-melting noncontinuous phase dispersed therein, said lower-melting continuous phase forming at least 50 percent by weight of the polymer blend and comprising a linear low density polyethylene polymer of a melt index of greater than 10 and a density of 0.945 g/cc or less and said at least one higher-melting noncontinuous phase comprising a polypropylene polymer with melt flow rate of greater than 20 g/10 min.

2. The multicomponent fiber of claim 1, wherein said fibers are bicomponent fibers with the polymer components arranged in a sheath-core structured domain, wherein said sheath component comprises said multipolymer blend.

3. The multicomponent fiber of claim 1, wherein said lower-melting continuous phase comprises a linear low density polyethylene having a density of 0.90–0.945 g/cc and a melt index of greater than 25.

4. The multicomponent fiber of claim 1, wherein lower-melting continuous phase comprises a linear low density polyethylene having a density of 0.90–0.945 g/cc, and said at least one higher-melting noncontinuous phase comprises an isotactic polypropylene polymer with melt flow rate of at least 20 g/10 min.

5. The multicomponent fiber of claim 1, wherein said lower-melting polymer phase comprises linear low density polyethylene and said higher-melting polymer phase comprises an isotactic polypropylene with a melt flow rate greater than 30 g/10 minutes.

6. The multicomponent fiber of claim 1, wherein said lower-melting polymer phase comprises linear low density polyethylene with a melt index of greater than 30.

7. The multicomponent fiber of claim 1, wherein said lower-melting polymer phase comprises low pressure, solution process, linear short chain branched polyethylene with a melt index of greater than 30 and a density of 0.945 g/cc and said higher-melting polymer phase comprises isotactic polypropylene.

8. The multicomponent fiber of claim 1, wherein said lower-melting polymer phase comprises linear low density polyethylene with a melt index of 27 and said higher-melting polymer phase comprises an isotactic polypropylene with a melt flow rate of 35 g/10 minutes.

9. The multicomponent fiber of claim 1, wherein said fiber is selected from the group consisting of continuous filaments, staple fibers, and meltblown fibers.

10. A multicomponent fiber comprising at least two polymer components arranged in structured domains, at least one of said polymer components comprising a multipolymer blend of at least two different polyolefin polymers, said polymers being present as a lower-melting dominant continuous phase and at least one higher-melting noncontinuous phase dispersed therein, said lower-melting continuous phase forming at least 50 percent by weight of the polymer blend and comprising a polyethylene and said at least one higher-melting noncontinuous phase comprising at least one copolymer or terpolymer of propylene.

11. The multicomponent fiber of claim 10, wherein said fibers are bicomponent fibers with the polymer components arranged in a sheath-core structured domain, wherein said sheath component comprises said multipolymer blend.

12. The multicomponent fiber of claim 10, wherein said polyethylene comprises one or more polyethylenes selected from the group consisting of low density polyethylene, high pressure long chain branched polyethylene, linear low density polyethylene, high density polyethylene and copolymers thereof.

13. The multicomponent fiber of claim 10, wherein said copolymer or terpolymer of propylene comprises a random copolymer of propylene with ethylene.

14. The multicomponent fiber of claim 13, wherein said polyethylene is a linear low density polyethylene polymer with a density of 0.945 g/cc or less and said propylene polymer is a copolymer of propylene with up to 3 percent by weight ethylene.

15. The multicomponent fiber of claim 14, wherein said sheath domain comprises from 5 to 25 percent by weight ethylene propylene copolymer and 75 to 95 percent by weight linear low density polyethylene.

16. The multicomponent fiber of claim 11, wherein said fiber is selected from the group consisting of continuous filaments, staple fibers, and meltblown fibers.

17. A nonwoven fabric comprising a plurality of multicomponent fibers comprising at least two polymer components arranged in structured domains, at least one of said polymer components comprising a multipolymer blend of at least two different polyolefin polymers, said polymers being present as a lower-melting dominant continuous phase and at least one higher-melting noncontinuous phase dispersed therein, said lower-melting continuous phase forming at least 50 percent by weight of the polymer blend and comprising a linear low density polyethylene polymer of a melt index of greater than 10 and a density of 0.945 g/cc or less and said at least one higher-melting noncontinuous phase comprising a polypropylene polymer with melt flow rate of greater than 20 g/10 min., said fibers bonded by a plurality of bonds to form a coherent extensible nonwoven fabric.

18. The fabric of claim 17, wherein said fibers are bicomponent fibers with the polymer components arranged in a sheath-core structured domain, wherein said sheath component comprises said multipolymer blend.

19. The fabric of claim 17, wherein said fibers are selected from the group consisting of continuous filaments, staple fibers, and meltblown fibers.

20. The fabric of claim 17, wherein said fabric has a Taber surface abrasion value (rubber wheel) of greater than 10 cycles and an elongation at peak load in at least one of the machine direction or the cross-machine direction of at least 70 percent.

21. The fabric of claim 20, wherein said fabric has an elongation at peak load of at least 100 percent.

22. The fabric of claim 17, wherein said fibers are bonded to one another at discrete locations by thermal point bonds.

23. A nonwoven fabric comprising a plurality of multicomponent fibers comprising at least two polymer components arranged in structured domains, at least one one of said polymer components comprising a multipolymer blend of at least two different polyolefin polymers, said polymers being present as a lower-melting dominant continuous phase and at least one higher-melting noncontinuous phase dispersed therein, said lower-melting continuous phase forming at least 50 percent by weight of the polymer blend and comprising a polyethylene and said at least one higher-melting noncontinuous phase comprising at least one copolymer or terpolymer of propylene.

24. The fabric of claim 23, wherein said fibers are bicomponent fibers with the polymer components arranged in a sheath-core structured domain, wherein said sheath component comprises said multipolymer blend.

25. The fabric of claim 23, wherein said fibers are selected from the group consisting of continuous filaments, staple fibers, and meltblown fibers.

26. The fabric of claim 23, wherein said fabric has a Taber surface abrasion value (rubber wheel) of greater than 10 cycles and an elongation at peak load in at least one of the machine direction or the cross-machine direction of at least 70 percent.

27. The fabric of claim 26, wherein said fabric has an elongation at peak load of at least 100 percent.

28. The fabric of claim 23, wherein said fibers are bonded to one another at discrete locations by thermal point bonds.

29. A composite nonwoven fabric of at least two layers, said composite fabric comprising a first layer containing a plurality of multicomponent fibers comprising at least two polymer components arranged in structured domains, at least one of said polymer components comprising a multipolymer blend of at least two different polyolefin polymers, said polymers being present as a lower-melting dominant continuous phase and at least one higher-melting noncontinuous phase dispersed therein, said lower-melting continuous phase forming at least 50 percent by weight of the polymer blend and comprising a linear low density polyethylene polymer of a melt index of greater than 10 and a density of 0.945 g/cc or less and said at least one higher-melting noncontinuous phase comprising a polypropylene polymer with melt flow rate of greater than 20 g/10 min., said fibers bonded by a plurality of bonds to form a coherent nonwoven web, said composite fabric comprising a second layer attached to said first layer.

30. The composite nonwoven fabric of claim 29, further comprising an adhesive layer disposed between said coherent nonwoven web and said second layer laminating the coherent nonwoven web to said second layer to form the composite fabric.

31. The composite nonwoven fabric of claim 29, wherein said coherent nonwoven web comprises a thermally bonded spunbond nonwoven web of randomly arranged substantially continuous filaments.

32. The composite nonwoven fabric of claim 29, wherein said coherent nonwoven web comprises a thermally bonded carded web of staple fibers.

33. The composite nonwoven fabric of claim 29, wherein said coherent nonwoven web additionally includes meltblown microfibers.

34. The composite nonwoven fabric of claim 29, wherein said second layer comprises a web selected from the group consisting of spunbonded webs of continuous filaments, webs of meltblown microfibers, elastic webs, and polyolefin films.

35. A composite nonwoven fabric of at least two layers, said composite fabric composing a first layer containing a plurality of multicomponent fibers comprising at least two polymer components arranged in structured domains, at least one of said polymer components comprising a multi-polymer blend of at least two different polyolefin polymers, said polymers being present as a lower-melting dominant continuous phase and at least one higher-melting noncontinuous phase dispersed therein, said lower-melting continuous phase forming at least 50 percent by weight of the polymer blend and comprising a polyethylene and said at least one higher-melting noncontinuous phase comprising at least one copolymer or terpolymer of propylene, said fibers bonded by a plurality of bonds to form a coherent nonwoven web, said composite fabric comprising a second layer attached to said first layer.

36. The composite nonwoven fabric of claim 35, further comprising an adhesive layer disposed between said coherent nonwoven web and said second layer laminating the coherent nonwoven web to said second layer to form the composite fabric.

37. The composite nonwoven fabric of claim 35, wherein said coherent nonwoven web comprises a thermally bonded spunbond nonwoven web of randomly arranged substantially continuous filaments.

38. The composite nonwoven fabric of claim 35, wherein said coherent nonwoven web comprises a thermally bonded carded web of staple fibers.

39. The composite nonwoven fabric of claim 35, wherein said coherent nonwoven web additionally includes meltblown microfibers.

40. The composite nonwoven fabric of claim 35, wherein said second layer comprises a web selected from the group consisting of spunbonded webs of continuous filaments, webs of meltblown microfibers, elastic webs, and polyolefin films.

41. A disposable absorbent personal care product comprising a plurality of layers, at least one of said layers comprising a nonwoven fabric comprised of fibrous material in the form of continuous filaments or staple fibers comprising first and second polymer components, at least one of said first and second polymer components comprising a multipolymer blend of at least two different polyolefin polymers, said polymers being present as a lower-melting dominant continuous phase and at least one higher-melting noncontinuous phase dispersed therein, said lower-melting continuous phase forming at least 50 percent by weight of the polymer blend and comprising a linear low density polyethylene polymer of a melt index of greater than 10 and a density of 0.945 g/cc or less and said at least one higher-melting noncontinuous phase comprising a polypropylene polymer with melt flow rate of greater than 20 g/10 min., said fibers bonded by a plurality of bonds to form a coherent nonwoven web.

42. The disposable personal care product of claim 41, wherein the fibrous material comprises continuous filaments randomly arranged and bonded to one another at discrete locations to form a nonwoven spunbonded fabric.

43. The disposable personal care product of claim 41, wherein said disposable absorbent personal care product is a diaper, incontinence pad, or sanitary napkin.

44. A disposable absorbent personal care product comprising a plurality of layers, at least one of said layers comprising a nonwoven fabric comprised of fibrous material in the form of continuous filaments or staple fibers comprising first and second polymer components, at least one of said first and second polymer components comprising a multipolymer blend of at least two different polyolefin polymers, said polymers being present as a lower-melting dominant continuous phase and at least one higher-melting noncontinuous phase dispersed therein, said lower-melting continuous phase forming at least 50 percent by weight of the polymer blend and comprising a polyethylene and said at least one higher-melting noncontinuous phase comprising at least one copolymer or terpolymer of propylene, said fibers bonded by a plurality of bonds to form a coherent nonwoven web.

45. The disposable personal care product of claim 44, wherein the fibrous material comprises continuous filaments randomly arranged and bonded to one another at discrete locations to form a nonwoven spunbonded fabric.

46. The disposable personal care product of claim 44, wherein said disposable absorbent personal care product is a diaper, incontinence pad, or sanitary napkin.

* * * * *